(12) United States Patent
Aebi et al.

(10) Patent No.: US 9,790,200 B2
(45) Date of Patent: Oct. 17, 2017

(54) DIHYDROQUINOLINE PYRAZOLYL COMPOUNDS

(71) Applicant: Hoffmann-La Roche Inc., Little Falls, NJ (US)

(72) Inventors: Johannes Aebi, Binningen (CH); Kurt Amrein, Itingen (CH); Benoit Hornsperger, Altkirch (FR); Bernd Kuhn, Reinach BL (CH); Hans P. Maerki, Basel (CH); Rainer E. Martin, Basel (CH); Alexander V. Mayweg, Basel (CH); Xuefei Tan, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/498,957

(22) Filed: Apr. 27, 2017

(65) Prior Publication Data

US 2017/0226079 A1    Aug. 10, 2017

Related U.S. Application Data

(63) Continuation of application No. PCT/EP2015/074774, filed on Oct. 26, 2015.

(51) Int. Cl.
*C07D 401/04*    (2006.01)
*C07D 401/14*    (2006.01)

(52) U.S. Cl.
CPC ......... *C07D 401/04* (2013.01); *C07D 401/14* (2013.01)

(58) Field of Classification Search
CPC ............................. C07D 401/04; C07D 401/14
See application file for complete search history.

(56) References Cited

U.S. PATENT DOCUMENTS 5,739,338 A * 4/1998 Beard .................. C07D 215/06
546/153

FOREIGN PATENT DOCUMENTS

| WO | 2009/135651 A1 | 11/2009 |
| WO | 2013/120771 A1 | 8/2013 |
| WO | 2013/166015 A1 | 11/2013 |
| WO | 2014/139981 A1 | 9/2014 |

OTHER PUBLICATIONS

Zimmer, Bloorg & Med Chem Lett, vol. 21, 186-190, 2011.*
ISR for PCT/EP2015/074774.

* cited by examiner

*Primary Examiner* — D M Seaman

(57) ABSTRACT

The invention provides novel compounds having the general formula (I)

(I)

wherein $R^1$, $R^2$, $R^3$, $R^4$, $R^5$, $R^6$, $R^7$, $R^8$, $R^9$, $R^{15}$, $R^{16}$, $R^{17}$ and n are as described herein, compositions including the compounds and methods of using the compounds.

19 Claims, No Drawings

DIHYDROQUINOLINE PYRAZOLYL COMPOUNDS

CROSS REFERENCE TO RELATED APPLICATIONS

This application is a continuation of International Application No. PCT/EP2015/074774 having an international filing date of Oct. 26, 2015 and which claims benefit under 35 U.S.C. §119 to International Application PCT/CN2014/090063 filed Oct. 31, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

BRIEF SUMMARY OF THE INVENTION

The present invention provides novel compounds of formula (I)

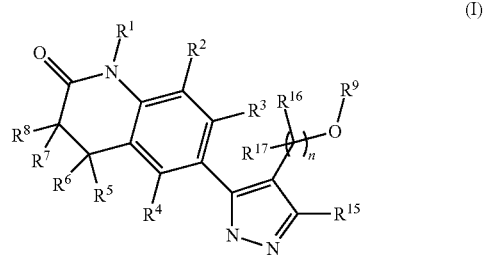

wherein
$R^1$, $R^5$, $R^6$, $R^7$ and $R^8$ are independently selected from H, alkyl, haloalkyl, cycloalkyl and halocycloalkyl;
$R^2$, $R^3$ and $R^4$ are independently selected from H, halogen, alkyl, haloalkyl, cycloalkyl and halocycloalkyl;
$R^9$ is alkylsulfanylalkyl, alkyl sulfonylalkyl, aryl, substituted aryl, arylalkyl, substituted arylalkyl, heteroaryl, substituted heteroaryl, hetroarylalkyl, substituted heteroarylalkyl or the group A, wherein substituted aryl, substituted arylalkyl, substituted heteroaryl and substituted heteroarylalkyl are substituted with one to three substituents selected from alkyl, halogen, haloalkyl, cycloalkyl, halocycloalkyl, cyano, alkoxy, haloalkoxy, alkylsulfanyl, haloalkylsulfanyl, alkylsulfonyl and haloalkylsulfonyl;

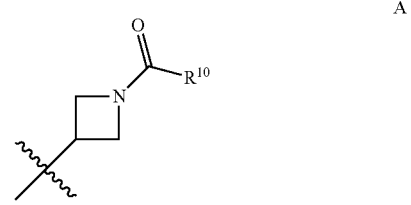

$R^{10}$ is pyrazolyl, substituted pyrazolyl, pyridinyl or substituted pyridinyl, wherein substituted pyrazolyl and substituted pyridinyl are substituted with one to three substituents selected from alkyl, halogen, haloalkyl, cycloalkyl and halocycloalkyl;
$R^{15}$ is H, alkyl, haloalkyl, cycloalkyl or halocycloalkyl;
$R^{16}$ and $R^{17}$ are independently selected from H, alkyl and cycloalkyl;
n is zero or 1;
and pharmaceutically acceptable salts thereof.

In another embodiment, the present inventions provide for pharmaceutical compositions comprising compounds of Formula I.

In another embodiment, the present invention provides aldosterone synthase inhibitors for therapy in a mammal useful for the treatment or prophylaxis of chronic kidney disease, congestive heart failure, hypertension, primary aldosteronism and Cushing syndrome.

In another embodiment, the present invention provides aldosterone synthase inhibitors for therapy in a mammal useful for the treatment of chronic kidney disease, congestive heart failure, hypertension, primary aldosteronism and Cushing syndrome.

DETAILED DESCRIPTION OF THE INVENTION

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYPB11B2 and present an improved selectivity towards CYP11B2 versus CYP11B1 combined with an improved metabolic stability.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkoxy" denotes a group of the formula R'—O—, wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl and isopropyl, n-butyl, iso-butyl, sec-butyl and ter-butyl. Particular alkyl group is methyl.

The term "alkylsulfanyl" denotes a group of the formula R'—S—, wherein R' is an alkyl group. Examples of alkylsulfanyl are groups wherein R' is methyl, ethyl, propyl and isopropyl, n-butyl, iso-butyl, sec-butyl and ter-butyl. Particular alkylsulfanyl is group wherein R' is methyl.

The term "alkylsulfanylalkyl" denotes an alkyl group wherein one of the hydrogen atoms of the alkyl group has been replaced an alkylsulfanyl group. Particular examples of alkylsulfanylalkyl groups are methylsulfanylethyl and methyl sulfanylpropanyl.

The term "alkylsulfonyl" denotes a group of the formula R'—S(O)$_2$—, wherein R' is an alkyl group. Examples of alkylsulfonyl are groups wherein R' is methyl, ethyl, propyl and isopropyl, n-butyl, iso-butyl, sec-butyl and ter-butyl. Particular alkylsulfonyl is group wherein R' is methyl.

The term "alkylsulfonylalkyl" denotes an alkyl group wherein one of the hydrogen atoms of the alkyl group has been replaced an alkylsulfonyl group. Particular examples of alkylsulfanylalkyl group is methylsulfonylethyl.

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "arylalkyl" denotes an alkyl group wherein one of the hydrogen atoms of the alkyl group has been replaced an aryl group. Particular arylalkyl group is phenylmethyl.

The term "cyano" denotes a —C≡T group.

The term "cycloalkyl" denotes a monovalent saturated monocyclic hydrocarbon group of 3 to 10 ring carbon atoms. In particular embodiments, cycloalkyl denotes a monovalent saturated monocyclic hydrocarbon group of 3 to 8 ring carbon atoms. Examples for cycloalkyl are cyclopropyl, cyclobutanyl, cyclopentyl, cyclohexyl or cycloheptyl. Particular cycloalkyl group is cyclopropyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "haloalkylsulfanyl" denotes a group of the formula —S—R', wherein R' is a haloalkyl group. Examples of haloalkylsulfanyl groups include groups of the formula —S—R', wherein R' is trifluoromethyl.

The term "haloalkylsulfonyl" denotes a group of the formula —S(O)$_2$—R', wherein R' is a haloalkyl group. Examples of haloalkylsulfonyl groups include groups of the formula —S(O)$_2$—R', wherein R' is trifluoromethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl include fluorocyclopropyl, difluorocyclopropyl, fluorocyclobutyl and difluorocyclobutyl.

The term "halogen" and "halo" are used interchangeably herein and denote fluoro, chloro, bromo, or iodo. Particular halogens are chloro and fluoro. Particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl are imidazolyl, oxazolyl, pyridinyl, pyrazinyl, pyrazolyl, pyridazinyl, pyrimidinyl, isoxazolyl. Particular heteroaryl is and pyrazolyl.

The term "heteroarylalkyl" denotes an alkyl group wherein one of the hydrogen atoms of the alkyl group has been replaced an aryl group. Particular heteroarylalkyl group is heteroarylmethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. μAdditionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H ("T"), $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resuting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Also a particular embodiment of the present invention are compounds according to formula (I) as described herein wherein $R^1$ is alkyl.

A particular embodiment of the present invention are compounds according to formula (I) as described herein, wherein $R^5$, $R^6$, $R^7$ and $R^8$ are H.

Another particular embodiment of the present invention are compounds according to formula (I) as described herein, wherein $R^2$ and $R^3$ are H Also an embodiment of the present invention are compounds according to formula (I) as described herein, wherein $R^4$ is H or halogen.

A more particular embodiment of the present invention are compounds according to formula (I) as described herein, wherein $R^4$ is H.

Another particular embodiment of the present invention are compounds according to formula (I) as described herein, wherein $R^{15}$ is H.

Also a particular embodiment of the present invention are compounds according to formula (I) as described herein, wherein $R^{16}$ and $R^{17}$ are H.

Another embodiment of the present invention are compounds according to formula (I) as described herein, wherein n is 0.

Another particular embodiment of the present invention is are compounds of formula (I) wherein $R^1$ is alkyl, $R^2$, $R^3$, $R^5$, $R^6$, $R^7$, $R^8$, $R^{15}$, $R^{16}$, and $R^{17}$ are H, $R^4$ is H or halogen and n is 0.

Another particular embodiment of the present invention are compounds according to formula (I) as described herein, wherein the heteroaryl group from $R^9$ is alkylsulfanylalkyl, alkylsulfonylalkyl, substituted aryl, substituted arylalkyl or the group A, wherein substituted aryl and substituted arylalkyl are substituted with one to three substituents selected from alkyl, halogen, cyano, alkoxy, alkylsulfanyl and alkylsulfonyl.

Another particular embodiment of the present invention is are compounds of formula (I) wherein $R^1$ is alkyl, $R^2$, $R^3$, $R^5$, $R^6$, $R^7$, $R^8$, $R^{15}$, $R^{16}$, and $R^{17}$ are H, $R^4$ is H or halogen and n is 0 and wherein the heteroaryl group from $R^9$ is alkylsulfanylalkyl, alkylsulfonylalkyl, substituted aryl, substituted arylalkyl or the group A, wherein substituted aryl and substituted arylalkyl are substituted with one to three substituents selected from alkyl, halogen, cyano, alkoxy, alkylsulfanyl and alkylsulfonyl.

Another embodiment of the present invention are compounds according to formula (I) as described herein, wherein $R^9$ is aryl substituted with one to three substituents selected from alkyl, halogen, cyano, alkoxy, alkylsulfanyl and alkylsulfonyl.

Another particular embodiment of the present invention is are compounds of formula (I) wherein $R^1$ is alkyl, $R^2$, $R^3$, $R^5$, $R^6$, $R^7$, $R^8$, $R^{15}$, $R^{16}$, and $R^{17}$ are H, $R^4$ is H or halogen and n is 0 and wherein $R^9$ is aryl substituted with one to three substituents selected from alkyl, halogen, cyano, alkoxy, alkylsulfanyl and alkylsulfonyl.

A particular embodiment of the present invention are compounds according to formula (I) as described herein, wherein $R^{12}$ is pyrazolyl substituted by alkyl.

A particular embodiment of the present invention are compounds according to formula (I) as described herein, wherein $R^{10}$ is pyrazolyl substituted by alkyl.

Another particular embodiment of the present invention is are compounds of formula (I) wherein $R^1$ is alkyl, $R^2$, $R^3$, $R^5$, $R^6$, $R^7$, $R^8$, $R^{15}$, $R^{16}$ and $R^{17}$ are H, $R^4$ is H or halogen and n is 0 and wherein $R^{10}$ is pyrazolyl substituted by one alkyl.

Another particular embodiment of the present invention is are compounds of formula (I) wherein $R^1$ is alkyl, $R^2$, $R^3$, $R^5$, $R^6$, $R^7$, $R^8$, $R^{15}$, $R^{16}$ and $R^{17}$ are H, $R^4$ is H or halogen and n is 0 and wherein $R^{10}$ is pyrazolyl substituted by pyridinyl substituted by one halogen.

Particular examples of compounds of formula (I) as described herein are selected from 4-[[5-(1-Methyl-2-oxo-3,4-dihydroquinolin-6-yl)-1H-pyrazol-4-yl]oxy]benzonitrile;

6-[4-(4-Chlorophenoxy)-1H-pyrazol-5-yl]-1-methyl-3,4-dihydroquinolin-2-one;

3-Methoxy-4-[[5-(1-methyl-2-oxo-3,4-dihydroquinolin-6-yl)-1H-pyrazol-4-yl]oxy]benzonitrile;

3-Chloro-4-[[5-(1-methyl-2-oxo-3,4-dihydroquinolin-6-yl)-1H-pyrazol-4-yl]oxy]benzonitrile;

2-Fluoro-4-[[5-(1-methyl-2-oxo-3,4-dihydroquinolin-6-yl)-1H-pyrazol-4-yl]oxy]benzonitrile;

2-Chloro-4-[[5-(1-methyl-2-oxo-3,4-dihydroquinolin-6-yl)-1H-pyrazol-4-yl]oxy]benzonitrile;

6-[4-(3-Chlorophenoxy)-1H-pyrazol-5-yl]-1-methyl-3,4-dihydroquinolin-2-one;

1-Methyl-6-[4-(4-methylsulfanylphenoxy)-1H-pyrazol-5-yl]-3,4-dihydroquinolin-2-one;

1-Methyl-6-[4-(3-methylsulfanylphenoxy)-1H-pyrazol-5-yl]-3,4-dihydroquinolin-2-one;

1-Methyl-6-[4-(3-methylsulfonylphenoxy)-1H-pyrazol-5-yl]-3,4-dihydroquinolin-2-one;

1-Methyl-6-[4-(4-methylsulfonylphenoxy)-1H-pyrazol-5-yl]-3,4-dihydroquinolin-2-one;

1-Methyl-6-[4-(2-methylsulfanylethoxymethyl)-1H-pyrazol-3-yl]-3,4-dihydroquinolin-2-one;

(rac)-1-Methyl-6-[4-(1-methylsulfanylpropan-2-yloxymethyl)-1H-pyrazol-3-yl]-3,4-dihydroquinolin-2-one;

1-Methyl-6-[4-(2-methylsulfonylethoxymethyl)-1H-pyrazol-3-yl]-3,4-dihydroquinolin-2-one;

6-[4-[(4-Methoxyphenyl)methoxy]-1H-pyrazol-3-yl]-1-methyl-3,4-dihydroquinolin-2-one;

6-[4-[[1-(3-Chloropyridine-2-carbonyl)azetidin-3-yl]oxymethyl]-1H-pyrazol-3-yl]-5-fluoro-1-methyl-3,4-dihydroquinolin-2-one;

5-Fluoro-1-methyl-6-[4-[[1-(1-methylpyrazole-4-carbonyl)azetidin-3-yl]oxymethyl]-1H-pyrazol-3-yl]-3,4-dihydroquinolin-2-one;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the persons skilled in the art such as e.g. chiral chromatography or crystallization. The substituents and indices used in the following description of the processes have the significance given herein.

The following abbreviations are used in the present text:

AcOH=acetic acid, BOC=t-butyloxycarbonyl, BuLi=butyllithium, CDI=1,1-carbonyldiimidazole, DCM=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Scheme 1

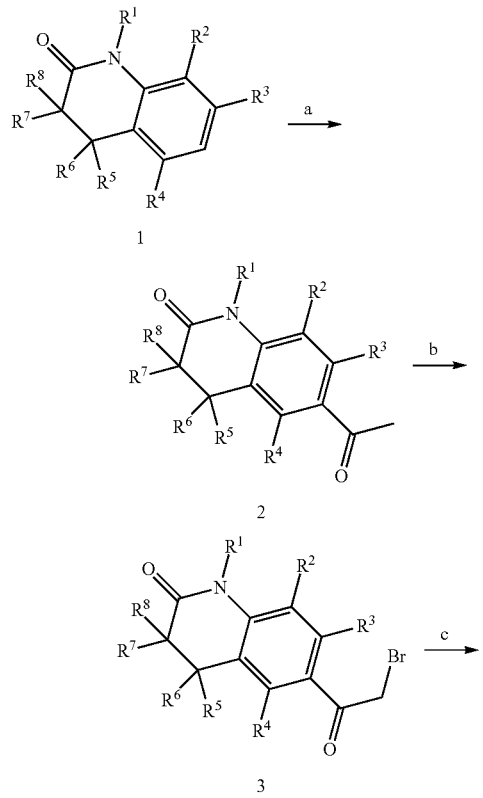

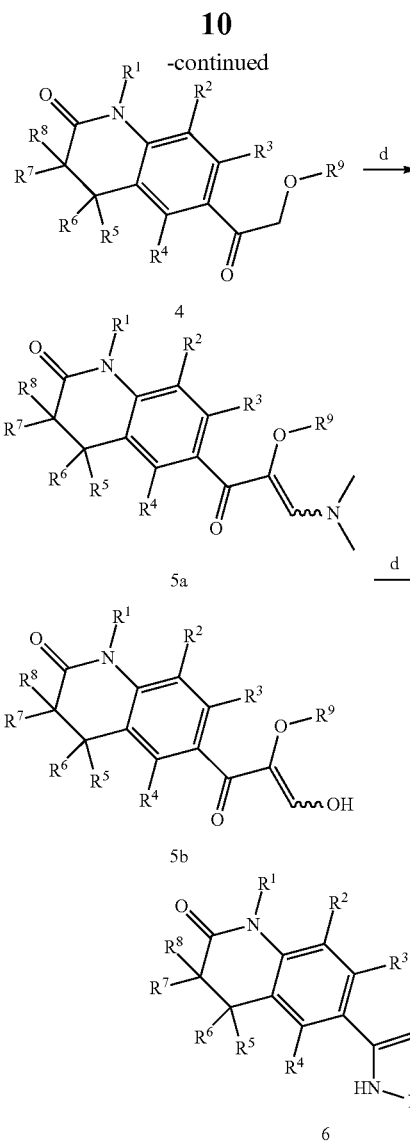

R$^9$ being aryl or heteroaryl

Acetyl compounds 2 (Scheme 1) can be prepared from dihydro-quinolin-one compounds 1 (known in the art or being prepared as described in Schemes 5 and 6) by Friedel-Crafts alkylation (e.g. by treatment with acetyl chloride, aluminum chloride in a solvent like carbon disulfide between room temperature and reflux) (step a). Subsequent halogenation at the CH$_3$—CO moiety (e.g. by reaction with trimethylphenylammonium-tribromide in dichloromethane at room temperature) gives bromo-methyl compounds 3 (step b). Reaction of bromo-methyl compounds 3 with suitable hydroxy-aryl or hydroxyl-heteroaryl compounds in the presence of a base like sodium, potassium or cesium carbonate or sodium hydride in solvents like tetrahydrofuran, dimethyl sulfoxide, N,N-dimethylformamide or 1,3-dimethyl-3,4,5,6-tetrahydro-2(1H)-pyrimidinone (DMPU) at temperatures between room temperature and about 100° C. gives (hetero)-aryloxy ketones 4 (step c). (Hetero)-Aryloxy-ketones 4 react with 1,1-dimethoxy-N,N-dimethylmethanamine in N,N-dimethylformamide at temperatures between about 50° C. and about 180° C. preferably with microwave heating to form dimethylamino adducts 5a or with a formic acid alkyl ester and a base like a sodium alkylate in an alcoholic solvent at temperatures between about 0° C. and room temperature to give hydroxy-alkene compounds 5b (step d). Dimethylamino adducts 5a or hydroxy-alkene compounds 5b react with hydrazine hydrate in the presence of an acid like e.g. aqueous hydrochloric acid in solvents like tetrahydrofuran, dioxane, methanol, ethanol or mixtures thereof at elevated temperatures e.g. between about 50° C. and the reflux temperature of the solvents to form pyrazole compounds 6 (step e).

Scheme 2

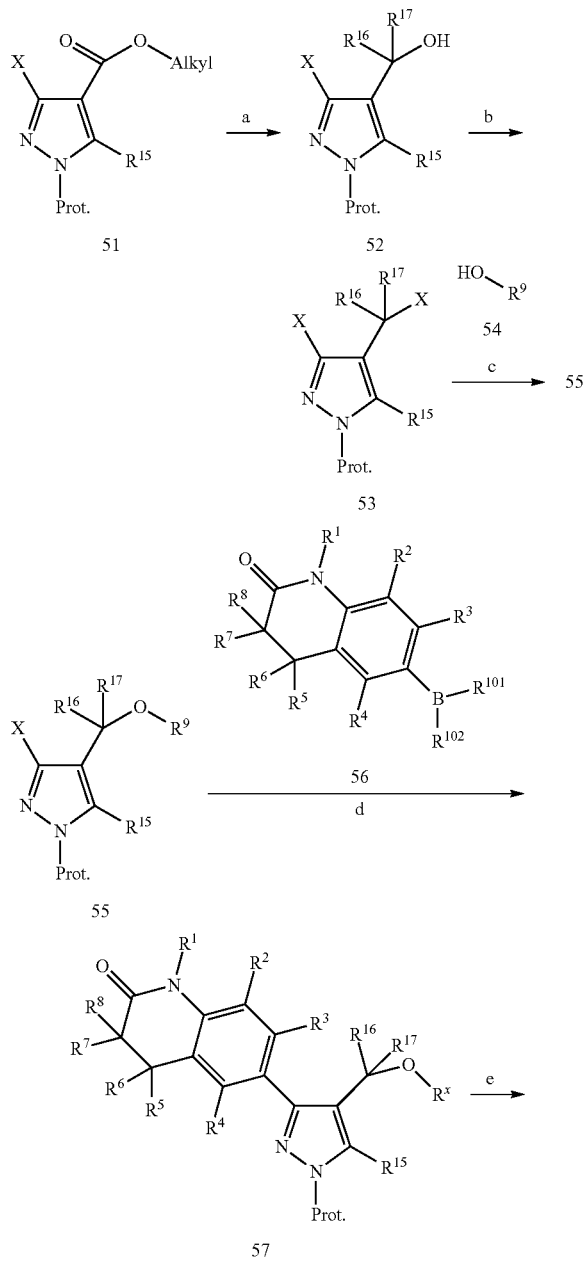

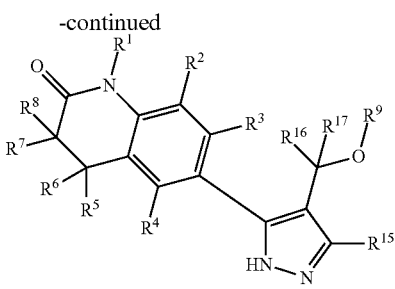

58

Prot. = Protecting Group
X is Halogen or OSO$_2$Alkyl/Aryl
R$^{101}$ and R$^{102}$ are both OH or, e.g. together with the boron atom to which they are attached form

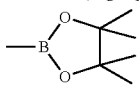

Halo-pyrazole ester compounds 51 (Scheme 2) carrying a suitable protecting group, as e.g. methoxybenzyl, tetrahydropyranyl, (2-trimethylsilyl)ethoxymethoxy, can be reduced to the corresponding primary alcohols 52 (R$^{16}$, R$^{17}$=H), e.g. by using lithium diisobutylaluminium hydride in a solvent like tetrahydrofuran in a temperature range between about −78° C. and room temperature. Alternatively, halo-pyrazole ester compounds 51 can be transformed into secondary or tertiary alcohols 52 by the following reaction sequence: i) saponification; ii) transformation into methoxy-N-methyl-amides (Weinreb amides); iii) conversion into ketones by reaction with Grignard reagents R$^{16}$MgX or lithium reagents R$^{16}$Li in solvents like THF in a temperature range between −78° C. and room temperature; iv) reduction with lithium diisobutylaluminium hydride or with sodium borohydride or reaction with Grignard reagents R$^{17}$MgX or lithium reagents R$^{17}$Li in solvents like THF in a temperature range between −78° C. and room temperature (step a).

Haloalkyl compounds 53 can be obtained from hydroxyalkyl compounds 52 by transformation of the OH into e.g. a chloro or bromo function e.g. by treatment with thionyl chloride or phosphorus tribromide in a solvent like DCM around room temperature, by reaction with methanesulfonyl chloride, Et$_3$N or 2,4,6-trimethylpyridine, DCM or DMF, and optionally LiCl or by reaction with triphenylphosphine/CCl$_4$ in CH$_3$CN, both procedures performed preferably between 0° C. and room temperature (step b). Halo-alkyl derivatives 53 react with OH-substituted compounds 54 in the presence of a base like sodium hydride or sodium or potassium tert-butoxide, in a solvent like DMF or THF preferably in a temperature range between 0° C. and about 80° C. giving ether linked halo-pyrazole compounds 55 (step c). Condensation of ether or amine linked halo-pyrazole compounds 55 with boronic acid or ester compounds 56 (known in the art or being prepared as described in Schemes 5 and 6) can be performed using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130°

C. leading to pyrazoles 57 (steps d). Removal of the protecting group in pyrazoles 57 then leads to pyrazoles 58 (e.g. treatment with trifluoroacetic acid under microwave conditions at temperatures around 100° C. can be used for removal of a p-methoxy-benzyl protecting group, treatment with 4M HCl in dioxane in MeOH around room temperature can be used for removal of a THP protecting group) (step e).

Oxyalkyl pyrazoles 152 (Scheme 4), optionally carrying a protecting group, can be prepared from pyrazoles 151 by reaction with an alkyl-halide, or an aralkyl-halide in a solvent like DMF in the presence of a base like sodium hydride and optionally a catalyst like tetrabutylammonium iodide preferably between 0° C. and room temperature (step a). Halogenation, e.g. iodination of oxyalkyl pyrazoles 152 (e.g. using N-iodo succinimide in a solvent like DMF at elevated temperature (up to 100° C.) gives halo-pyrazoles 153 (step b). Condensation of halo-pyrazoles 153 with boronic acid or ester compounds 56 can be performed using Suzuki conditions as already described in Scheme 2 (step c). Optional removal of the protecting group then leads to oxyalkyl pyrazoles 155 (step d).

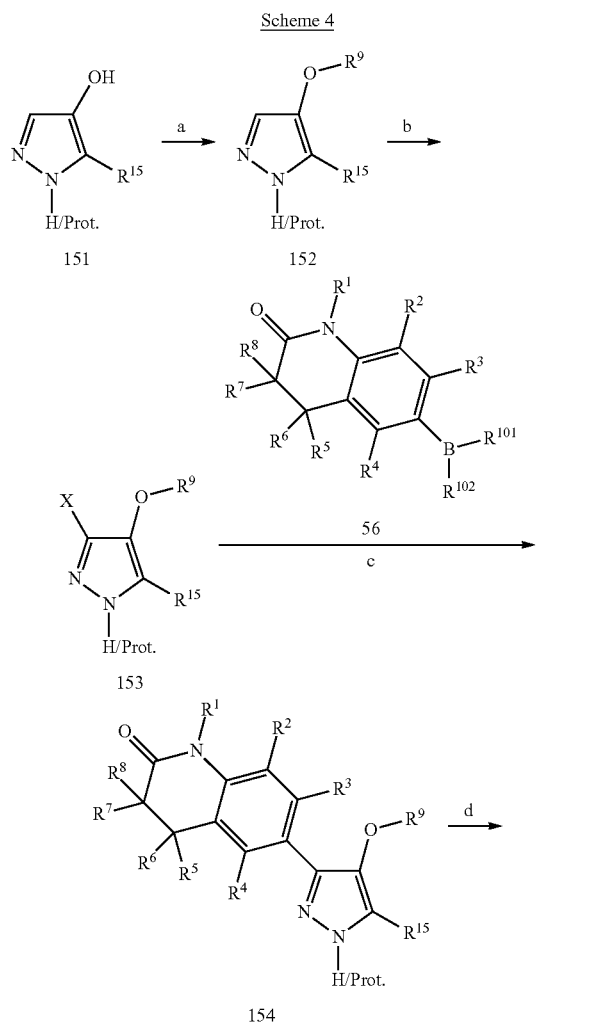

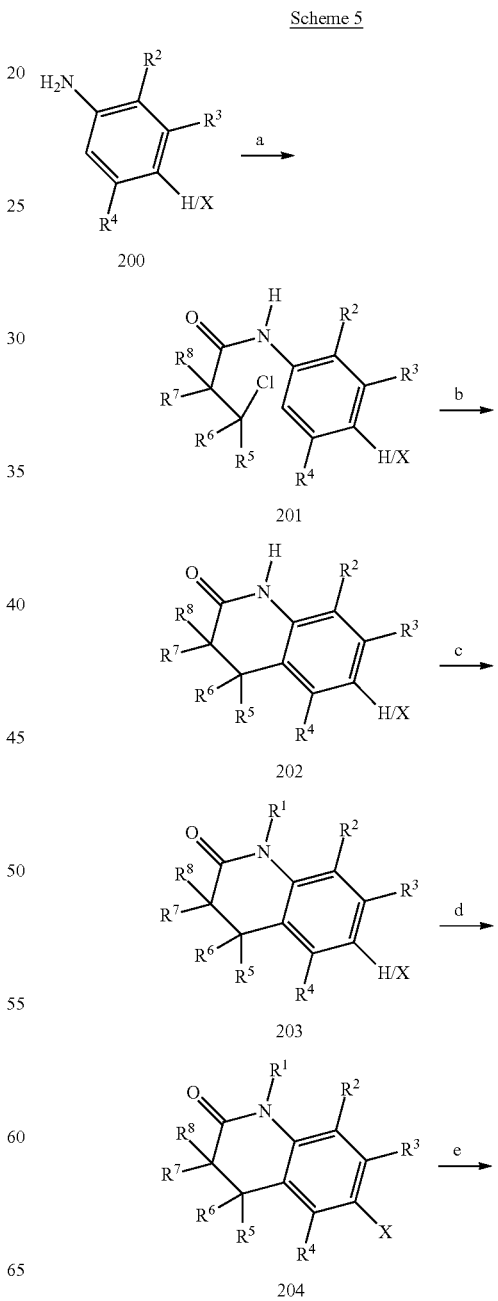

-continued

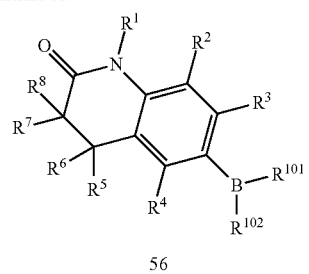

56

$R^{101}$ and $R^{102}$ are both OH or, e.g. together with the boron atom to which they are attached form

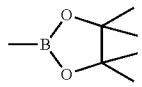

Chloropropionic acid anilides 201 (Scheme 5) can be prepared from chloro propionic acid chlorides and anilines 200 by reaction in a solvent like DCM in the presence of a base like pyridine preferably around room temperature (step a). Chloropropionic acid anilides 201 undergo ring closure to lactam compounds 202 when treated with $AlCl_3$ preferably without solvent at elevated temperatures of e.g. 100 to 150° C. (step b). Lactam compounds 202 can be alkylated at nitrogen using a base like sodium hydride or sodium or potassium tert-butoxide, followed by addition of an alkylating agent of formula wherein Y is halogen, tosylate or mesylate, in a solvent like DMF or THF preferably in a temperature range between 0° C. and about 80° C. giving N-alkylated lactams 203 (step c). Optional halogenation of N-alkylated lactams 203 can be performed e.g. by using N-bromo or N-chloro succinimide in solvents like DMF preferably around room temperature giving halo lactam compounds 204 with X equal to bromine or chlorine respectively (step d). Reaction of lactams 204 with e.g. 4,4,4',4',5,5,5',5'-octamethyl-2,2'-bi(1,3,2-dioxaborolane) in solvents like dimethylsulfoxide or dioxane in the presence of potassium acetate and catalysts like (1,1'-bis-diphenylphosphino)-ferrocene)palladium-(II)dichloride (1:1 complex with dichloromethane) at temperatures up to about 100° C. gives boronic ester compounds 56 (step e).

Scheme 6

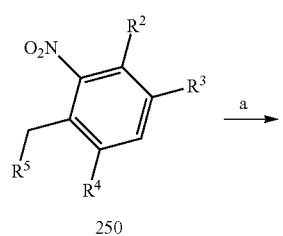

250

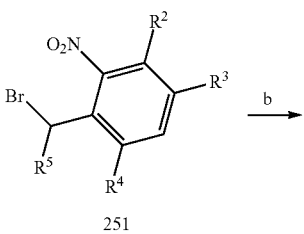

251

-continued

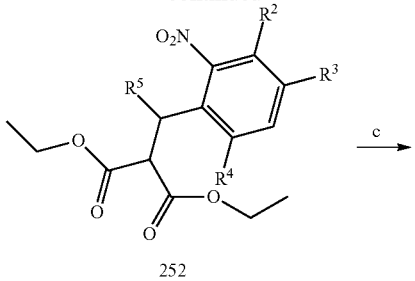

252

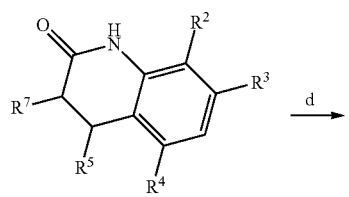

253

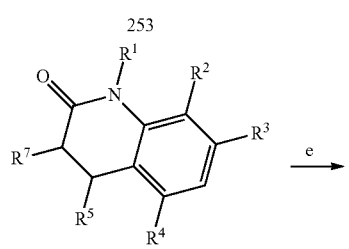

254

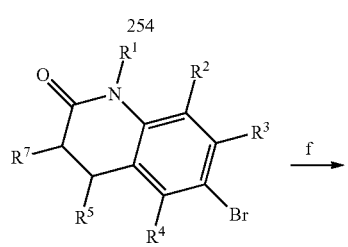

255

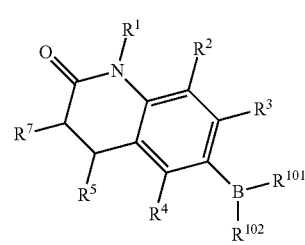

255

$R^{101}$ and $R^{102}$ are both OH or, e.g. together with the boron atom to which they are attached form

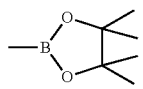

Treatment of nitro-benzene derivatives 250 e.g. with N-bromo succinimide, benzoyl peroxide (BPO) in a solvent like $CCl_4$ preferably at reflux gives bromo-methyl compounds 251 (Scheme 6, step a). Reaction of bromo-methyl compounds 251 and a suitable malonic ester derivative, preferable in the presence of cesium carbonate in a solvent like DMF between 0° C. and room temperature gives malonic ester adducts 252 (step b). Reduction of the nitro malonic ester derivatives 252 with e.g. stannous chloride dihydrate in 6 M aq. HCl at elevated temperature (e.g. 130° C.) directly leads to lactam compounds 253 (step c). Lactam compounds 253 can be alkylated at nitrogen, halogenated and converted into boronic ester compounds 256 as described for the preparation of compounds 56 (Scheme 5) (steps d, e, f).

Also an embodiment of the present invention is a process to prepare a compound of formula (I) as defined above comprising the reaction of a compound of formula (II) in the presence of hydrazine hydrate;

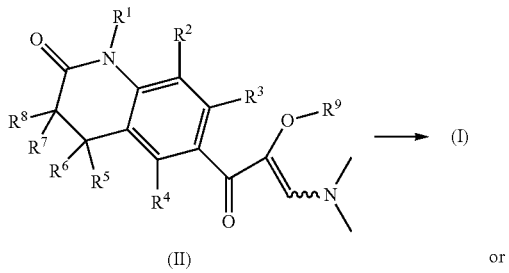

wherein $R^1$, $R^2$, $R^3$, $R^4$, $R^5$, $R^6$, $R^7$, $R^8$, $R^9$, $R^{15}$, $R^{16}$, $R^{17}$ are as described herein and n is zero.

In particular, in the presence of an acid, in particular aqueous hydrochloric acid, in solvents like tetrahydrofuran, dioxane, methanol, ethanol or mixtures thereof at elevated temperatures, in particular between about 50° C. and the reflux temperature of the solvents.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air. Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B2 nM | EC50 human CYP11B1 nM |
|---|---|---|
| 1 | 0.0133 | 0.8917 |
| 2 | 0.0155 | 0.3688 |
| 3 | 0.0943 | 1.6904 |
| 4 | 0.0403 | 2.7573 |
| 5 | 0.0581 | 0.7939 |
| 6 | 0.0246 | 1.1883 |
| 7 | 0.035 | 1.3932 |
| 8 | 0.0177 | 0.2975 |
| 9 | 0.0211 | 0.6635 |
| 10 | 0.06 | 4.0322 |
| 11 | 0.0197 | 0.652 |
| 12 | 0.0576 | 1.8512 |
| 13 | 0.1327 | 1.8098 |
| 14 | 0.502 | 22.1008 |
| 15 | 0.0017 | 0.0259 |
| 65 | 0.639 | 4.135 |
| 66 | 0.648 | >30 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1 but present an improved selectivity towards CYP11B2 versus CYP11B1.. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestionand the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the persons skilled in the art, such as e.g. chiral chromatography or crystallization.

EXAMPLES

All examples and intermediates were prepared under argon atmosphere if not specified otherwise.

Pyrazoles carrying a hydrogen substituent at any of the two nitrogen atoms and not symmetrical substituents at the 3 carbon atoms always exist in two tautomeric forms.

Formulas and names describe any of the two forms.

Intermediate A-1

4-[(Z and/or E)-2-(Dimethylamino)-1-(1-methyl-2-oxo-3,4-dihydroquinoline-6-carbonyl)vinyloxy]benzonitrile

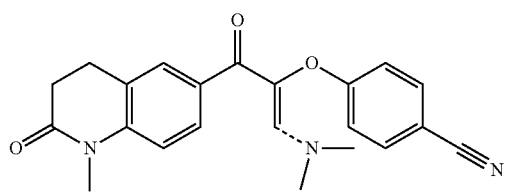

[A]4-(2-(1-Methyl-2-oxo-1,2,3,4-tetrahydroquinolin-6-yl)-2-oxoethoxy)benzonitrile

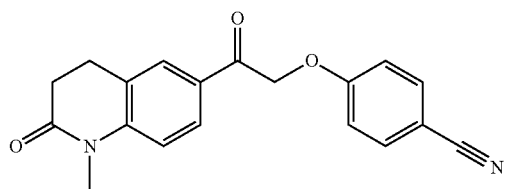 [SMILES: CN1C(=O)CCc2cc(C(=O)COc3ccc(C#N)cc3)ccc21]

To a solution of 6-(2-bromoacetyl)-1-methyl-3,4-dihydroquinolin-2-one (0.2 g, 0.709 mmol) in DMF (2 mL) was added 4-hydroxybenzonitrile (0.084 g, 0.709 mmol) followed by $K_2CO_3$ (0.196 g, 1.42 mmol) and the reaction mixture was then stirred at room temperature for 2 h. The mixture was diluted with EtOAc, poured into 1N aqueous HCl solution (5 mL) and the aqueous layer was extracted with EtOAc (2×15 mL). The organic layers were combined; the solid precipitate was filtered off and further dried to give a first batch of the title compound (0.135 g, 59%) as a colorless solid. The filtrate was dried over $Na_2SO_4$, filtered and evaporated. The residue was then purified by silica gel flash chromatography eluting with a 0 to 100% EtOAc-heptane gradient to give a second batch of the title compound (0.075 g, 33%) as a colorless solid. MS: 321.5 (M+H$^+$).

[B]4-[(Z and/or E)-2-(Dimethylamino)-1-(1-methyl-2-oxo-3,4-dihydroquinoline-6-carbonyl)vinyloxy]benzonitrile

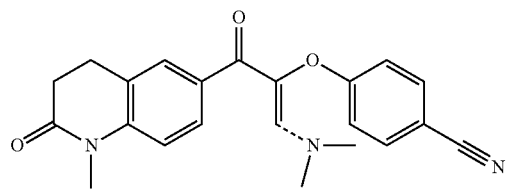

In a microwave vial, 4-(2-(1-methyl-2-oxo-1,2,3,4-tetrahydroquinolin-6-yl)-2-oxoethoxy)benzonitrile (0.210 g, 0.656 mmol) and 1,1-dimethoxy-N,N-dimethyl-methanamine (DMF-DMA) (0.094 g, 0.787 mmol) were dissolved in DMF (1 mL) and the reaction mixture was then heated to 110° C. for 2 times 30 min under microwave irradiation. The mixture was evaporated to dryness and the residue purified by silica gel flash chromatography eluting with a 0 to 5% MeOH-dichloromethane gradient to give the title compound (0.216 g, 88%) as a light brown solid. MS: 376.5 (M+H$^+$).

Intermediate A-2

(rac)-1-Methyl-6-[4-(2-methylsulfanylethoxymethyl)-1-tetrahydropyran-2-yl-pyrazol-3-yl]-3,4-dihydroquinolin-2-one

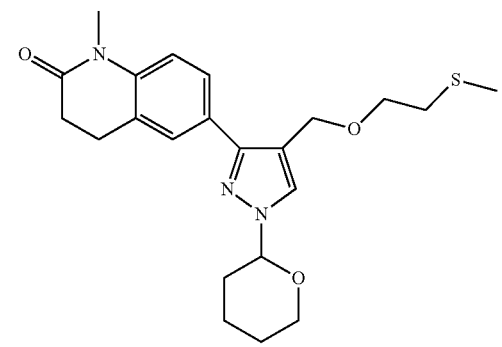 [SMILES: CSCCOCc1cn(C2CCCCO2)nc1-c1ccc2c(c1)CCC(=O)N2C]

[A] (rac)-Ethyl 3-iodo-1-(tetrahydro-2H-pyran-2-yl)-1H-pyrazole-4-carboxylate

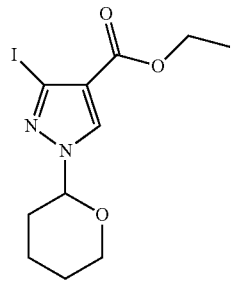 [SMILES: CCOC(=O)c1cn(C2CCCCO2)nc1I]

To a solution of ethyl 3-iodo-1H-pyrazole-4-carboxylate (0.4 g, 1.5 mmol) in DCM (6 mL) was added 3,4-dihydro-2H-pyran (0.152 g, 1.8 mmol) followed by p-toluenesulfonic acid monohydrate (0.029 g, 0.15 mmol) and the reaction mixture was then stirred at room temperature for 3 h. The mixture was diluted with DCM, poured into water (5 mL) and the aqueous layer was extracted with EtOAc (2×20 mL). The combined organics were washed with brine, dried over Na$_2$SO$_4$, filtered and evaporated. The residue was then purified by silica gel flash chromatography eluting with a 10 to 50% EtOAc-heptane gradient to give the title compound (0.526 g, 99%) as colorless oil.

[B] (rac)-(3-Iodo-1-(tetrahydro-2H-pyran-2-yl)-1H-pyrazol-4-yl)methanol

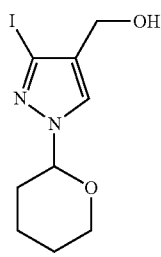

To a solution of (rac)-ethyl 3-iodo-1-(tetrahydro-2H-pyran-2-yl)-1H-pyrazole-4-carboxylate (0.526 g, 1.5 mmol) in THF (5 mL) cooled to −78° C. was added a 1M DIBAL-H solution in THF (3 mL, 3 mmol) dropwise and the reaction mixture was stirred at this temperature for 30 min. The mixture was then allowed to slowly warm up to 0° C. and stirring was continued at this temperature for 5 h. The mixture was quenched by drop wise addition of a 1N aqueous HCl solution (5 mL) and the resulting solution was then extracted with EtOAc (2×25 mL). The combined organics were washed with brine, dried over Na$_2$SO$_4$, filtered and evaporated. The residue was then purified by silica gel flash chromatography eluting with a 0 to 100% EtOAc-heptane gradient to give the title compound (0.309 g, 67%) as colorless oil. MS: 309.0 (M+H$^+$).

[C] (rac)-4-(Chloromethyl)-3-iodo-1-(tetrahydro-2H-pyran-2-yl)-1H-pyrazole

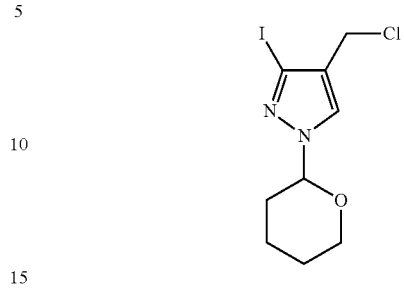

To a solution of (rac)-(3-iodo-1-(tetrahydro-2H-pyran-2-yl)-1H-pyrazol-4-yl)methanol (0.309 g, 1.0 mmol) in DMF (3 mL) cooled to 0° C. were added methanesulfonyl chloride (0.172 g, 1.5 mmol) and 2,4,6-trimethylpyridine (0.194 g, 1.6 mmol). The reaction mixture was then stirred for 10 min before lithium chloride (0.085 g, 2.01 mmol) was added and stirring was continued at room temperature for 4 h. The mixture was diluted with EtOAc, poured into water (5 mL) and the aqueous layer was extracted with EtOAc (2×15 mL). The combined organics were washed with brine, dried over Na$_2$SO$_4$, filtered and evaporated. The residue was then purified by silica gel flash chromatography eluting with a 0 to 70% EtOAc-heptane gradient to give the title compound (0.25 g, 75%) as colorless oil. MS: 242.9 (M-THP+H$^+$).

[D] (rac)-3-Iodo-4-((2-(methylthio)ethoxy)methyl)-1-(tetrahydro-2H-pyran-2-yl)-1H-pyrazole

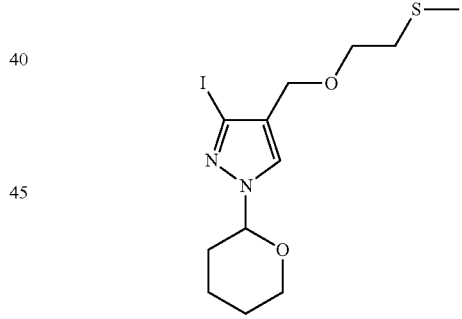

To a suspension of NaH, 60% in mineral oil (0.006 g, 0.161 mmol), in DMF (0.5 mL) cooled to 0° C. was added 2-(methylthio)ethanol (0.014 g, 0.153 mmol) and the reaction mixture was stirred for 30 min. Then, (rac)-4-(chloromethyl)-3-iodo-1-(tetrahydro-2H-pyran-2-yl)-1H-pyrazole (0.05 g, 0.153 mmol) was added and stirring was continued at room temperature overnight. The mixture was diluted with EtOAc, poured into 1N aqueous HCl solution (5 mL) and the aqueous layer was extracted with EtOAc (2×10 mL). The combined organics were washed with brine, dried over Na$_2$SO$_4$, filtered and evaporated. The residue was then purified by silica gel flash chromatography eluting with a 0 to 50% EtOAc-heptane gradient to give the title compound (0.02 g, 34%) as colorless oil. MS: 299.0 (M-THP+H$^+$).

[E] (rac)-1-Methyl-6-[4-(2-methylsulfanylethoxymethyl)-1-tetrahydropyran-2-yl-pyrazol-3-yl]-3,4-dihydroquinolin-2-one

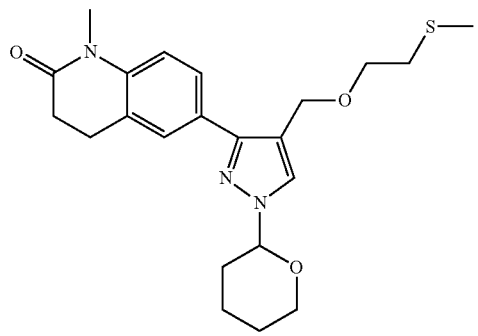 [SMILES: CSCCOCc1cn(C2CCCCO2)nc1-c1ccc2c(c1)CCC(=O)N2C]

To a solution of (rac)-3-iodo-4-((2-(methylthio)ethoxy)methyl)-1-(tetrahydro-2H-pyran-2-yl)-1H-pyrazole (0.02 g, 0.052 mmol) in DMF (0.5 mL) were added 1-methyl-6-(4,4,5,5-tetramethyl-1,3,2-dioxaborolan-2-yl)-3,4-dihydroquinolin-2(1H)-one (0.015 g, 0.052 mmol, Intermediate A-3), bis(diphenylphosphino)ferrocenedichloropalladium (II) (0.004 g, 0.005 mmol) and a 1M aqueous Na$_2$CO$_3$ solution (0.157 mL, 0.157 mmol). The reaction mixture was then heated to 100° C. for 15 min under microwave irradiation. The mixture was poured into water (2 mL) and extracted with EtOAc (2×5 mL). The combined organics were washed with brine, dried over Na$_2$SO$_4$, filtered and evaporated. The residue was purified by silica gel flash chromatography eluting with a 10 to 100% EtOAc-heptane gradient to give the title compound (0.015 g, 69%) as light brown oil. MS: 416.2 (M+H$^+$).

Intermediate A-3

1-Methyl-6-(4,4,5,5-tetramethyl-1,3,2-dioxaborolan-2-yl)-3,4-dihydroquinolin-2-one

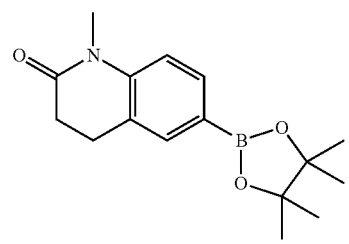 [SMILES: CN1C(=O)CCc2cc(B3OC(C)(C)C(C)(C)O3)ccc21]

[A] 6-Bromo-1-methyl-3,4-dihydroquinolin-2-one

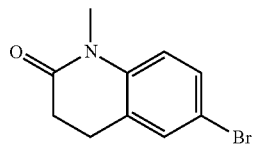

To a solution of 6-bromo-3,4-dihydro-1H-quinolin-2-one (5 g, 22.1 mmol) in DMF (100 mL) cooled to 0° C. was added potassium tert-butoxide (4.96 g, 44.2 mmol) portion wise and the reaction mixture was stirred at 0° C. for 15 min. Then, methyl iodide (4.08 g, 28.8 mmol) was added and the reaction mixture allowed to warm up to room temperature and stirring was continued overnight. More methyl iodide (1.25 g, 8.86 mmol) was added and the reaction mixture was heated to 40° C. until completion of the reaction. The mixture was diluted with EtOAc, poured into 100 mL of 1N HCl and the aqueous phase was extracted with EtOAc (2×200 mL). The combined organics were washed with brine, dried over anhy. Na$_2$SO$_4$, filtered and evaporated to dryness. The residue was purified by silica gel flash chromatography eluting with a 0 to 30% EtOAc-heptane gradient to give the title compound (4.23 g, 80%) as an off white solid. MS: 240.0, 242.1 (M+H$^-$).

[B] 1-Methyl-6-(4,4,5,5-tetramethyl-1,3,2-dioxaborolan-2-yl)-3,4-dihydroquinolin-2-one

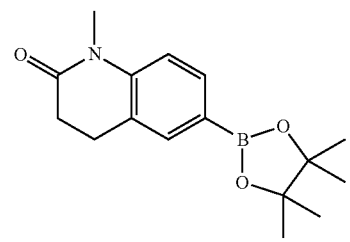

A flask was charged with 6-bromo-1-methyl-3,4-dihydroquinolin-2-one (3 g, 12.5 mmol), 4,4,4',4',5,5,5',5'-octamethyl-2,2'-bi(1,3,2-dioxaborolane) (3.81 g, 15.0 mmol), potassium acetate (3.68 g, 37.5 mmol) and dioxane (48 mL). The mixture was purged with Ar, then dichloro[1,1'-bis(diphenylphosphino)-ferrocene]palladium(II) dichloromethane complex (1:1) [PdCl$_2$(DPPF) dichloromethane adduct] (457 mg, 0.560 mmol) was added and the resulting mixture was heated to 80° C. overnight. The reaction mixture was diluted with EtOAc, filtered through Celite and washed with EtOAc (2×150 mL). The resulting filtrate was washed with brine, dried over anhy. Na$_2$SO$_4$, filtered and evaporated to dryness. The residue was purified by silica gel flash chromatography eluting with a 0 to 40% EtOAc-heptane gradient to give the title compound (2.63 g, 73%) as an off white solid. MS: 288.0 (M+H$^+$).

Intermediate A-4

7-Fluoro-1-methyl-6-(4,4,5,5-tetramethyl-1,3,2-dioxaborolan-2-yl)-3,4-dihydroquinolin-2-one

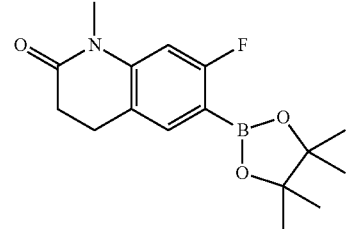 [SMILES: CN1C(=O)CCc2cc(B3OC(C)(C)C(C)(C)O3)c(F)cc21]

[A] 3-Chloro-N-(3-fluoro-phenyl)-propionamide

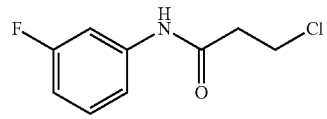 [SMILES: O=C(CCCl)Nc1cccc(F)c1]

To a solution of 3-fluoroaniline (10 mL, 104.02 mmol) in DCM (100 mL) was added pyridine (21 mL, 260.2 mmol) and 3-chloropropionyl chloride (12 mL, 124.4 mmol). The reaction mixture was stirred for 3 h at room temperature until all starting materials had disappeared as shown by LC-MS analysis. The reaction mixture was then diluted with H$_2$O and extracted with EtOAc. The organic layer was dried over anhy. Na$_2$SO$_4$ and concentrated in vacuo to afford the title compound as a solid. It was used in the next step without further purification.

[B] 7-Fluoro-3,4-dihydro-1H-quinolin-2-one

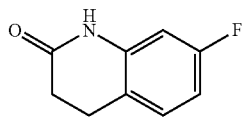 [SMILES: O=C1CCc2ccc(F)cc2N1]

A flame-dried 50-mL flask equipped with a magnetic stirring bar was charged with 3-chloro-N-(3-fluoro-phenyl)-propionamide (10 g, 49.6 mmol) and AlCl$_3$ (23.1 g, 173.6 mmol). On a pre-heated oil bath, the flask was heated to 120~125° C. for 2 h until LC-MS indicated the reaction was complete. After cooling to room temperature, the mixture was treated slowly with ice-water. After extraction with EtOAc, combined organics were washed with water and brine in sequence. The organic layer was dried over anhy. Na$_2$SO$_4$, filtered and concentrated in vacuo to afford a white solid (7.63 g, 93.2%).

[C]
7-Fluoro-1-methyl-3,4-dihydro-1H-quinolin-2-one

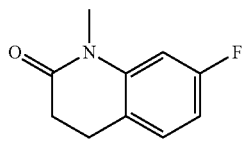

To an ice cold solution of 7-fluoro-3,4-dihydro-1H-quinolin-2-one (16.5 g, 0.1 mol) in DMF (200 mL) was added potassium tert-butoxide (22.4 g, 0.2 mol) in 2 portions. The reaction mixture was stirred at 0° C. for 30 min before methyl iodide (25.4 g, 0.18 mol) was added. After the addition, the reaction mixture was allowed to warm up to room temperature slowly and stirred at room temperature overnight. It was then diluted with EtOAc (500 mL) and poured into 200 mL of 1 N aq. HCl. After extraction with EtOAc (3×200 mL), the combined organics were washed with brine, dried over anhy. Na$_2$SO$_4$, filtered and concentrated in vacuo to give the crude title compound as oil (16.0 g, 89%). It was used in the next step without further purification.

[D] 6-Bromo-7-fluoro-1-methyl-3,4-dihydro-1H-quinolin-2-one

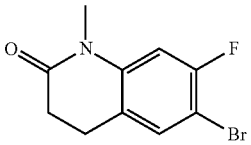

A mixture of 7-fluoro-1-methyl-3,4-dihydroquinolin-2-one (2.56 g, 0.014 mol) and NBS (3.0 g, 0.017 mol) in DMF (30 mL) was stirred for 12 h at 25° C. The reaction solution was diluted with H$_2$O (80 mL), and extracted with EtOAc (3×100 mL). The combined organics were washed by brine (3×100 mL), dried over anhy. Na$_2$SO$_4$ and concentrated in vacuo to give the title compound (1.5 g, 42%) as white foam. MS: 258.0, 259.9 (M+H$^+$).

[E] 7-Fluoro-1-methyl-6-(4,4,5,5-tetramethyl-[1,3,2]dioxaborolan-2-yl)-3,4-dihydro-1H-quinolin-2-one

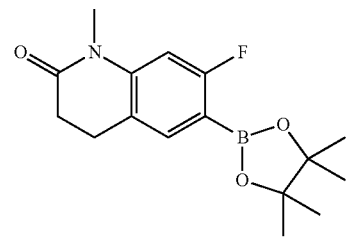 [SMILES: CN1C(=O)CCc2cc(B3OC(C)(C)C(C)(C)O3)c(F)cc21]

In analogy to the procedure described for the preparation of intermediates A-3[B], 6-bromo-7-fluoro-1-methyl-3,4-dihydro-1H-quinolin-2-one was reacted with 4,4,4',4',5,5,5',5'-octamethyl-2,2'-bi(1,3,2-dioxaborolane) in presence of potassium acetate and PdCl$_2$(DPPF)-CH$_2$Cl$_2$ to give the title compound as a white solid. MS: 306.1 (M+H$^+$).

Intermediate A-5

8-Chloro-1-methyl-6-(4,4,5,5-tetramethyl-1,3,2-dioxaborolan-2-yl)-3,4-dihydroquinolin-2-one

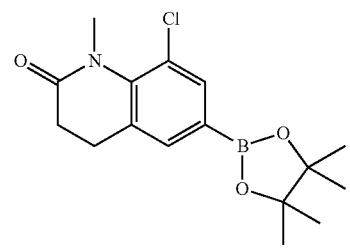 [SMILES: CN1C(=O)CCc2cc(B3OC(C)(C)C(C)(C)O3)cc(Cl)c21]

[A]
N-(4-Bromo-2-chloro-phenyl)-3-chloro-propionamide

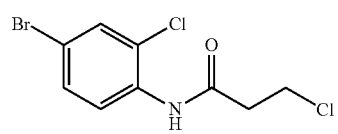 [SMILES: O=C(CCCl)Nc1ccc(Br)cc1Cl]

To a solution of 4-bromo-2-chloro-phenylamine (32 g, 0.15 mol) and pyridine (13.45 g, 0.17 mol) in DCM (200 mL) was added 3-chloropropionyl chloride (21.65 g, 0.17 mol) dropwise at 15° C. After stirring at room temperature for 1 hour, the mixture was washed with water and then aqueous 2N HCl. The organic layer was dried over anhy. Na$_2$SO$_4$, filtered, and concentrated in vacuo to afford title compound (10.9 g, 90%) as a white solid.

[B] 6-Bromo-8-chloro-3,4-dihydro-1H-quinolin-2-one

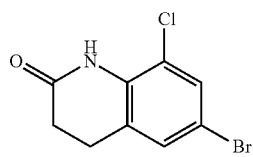 [SMILES: O=C1CCc2cc(Br)cc(Cl)c2N1]

A flame-dried 500-mL flask equipped with a magnetic stirring bar was charged with N-(4-bromo-2-chloro-phenyl)-3-chloro-propionamide (29.7 g, 0.1 mol) and aluminium chloride (53.3 g, 0.4 mol). In a pre-heated oil bath, the flask was heated to 140° C. for 1 h. After cooling to room temperature, the mixture was treated slowly with ice-water and extracted with EtOAc. The organic layer was washed with water and brine in sequence, dried over anhy. Na₂SO₄, filtered, and concentrated in vacuo. The resulting residue was then purified by silica gel flash chromatography (30% ethyl acetate in hexane) to afford the title compound (7.0 g, 27%) as a white solid.

[C] 6-Bromo-8-chloro-1-methyl-3,4-dihydro-1H-quinolin-2-one

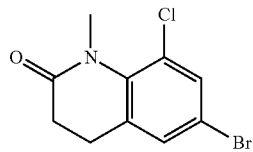

A solution of 6-bromo-8-chloro-3,4-dihydro-1H-quinolin-2-one (7.0 g, 26.9 mmol) in DMF (100 mL) was treated with potassium tert-butoxide (6.0 g, 53.8 mmol) at 0° C. portion wise. The resulting mixture was stirred at 0° C. for 30 min before methyl iodide (5.0 g, 35.0 mmol) was added. After stirring for 12 h, the reaction mixture was treated with water, extracted with EtOAc. The organic layer was washed with water and brine in sequence, and dried over anhy. Na₂SO₄. After removal of solvent under reduced pressure, the crude product (3.3 g, 45%) was obtained as a white solid.

[D] 8-Chloro-1-methyl-6-(4,4,5,5-tetramethyl-[1,3,2]dioxaborolan-2-yl)-3,4-dihydro-1H-quinolin-2-one

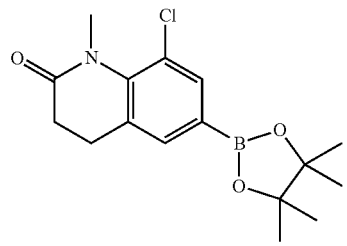 [SMILES: CN1C(=O)CCc2cc(B3OC(C)(C)C(C)(C)O3)cc(Cl)c21]

A mixture of 6-bromo-8-chloro-1-methyl-3,4-dihydro-1H-quinolin-2-one (0.23 g, 0.84 mmol), bis(pinacolato)diboron (0.255 g, 1.01 mmol), 1,1'-bis(diphenylphosphino)-ferrocene-dichloropalladium (II), dichloromethane complex (1:1) (30.7 mg, 0.04 mmol) and potassium acetate (0.247 g, 2.52 mmol) in dioxane (5 mL) was heated in a microwave at 80° C. overnight. After dilution with EtOAc, the organic layer was washed with water, dried over anhy. Na₂SO₄ and concentrated in vacuo. The residue was then purified by silica gel flash chromatography (30% ethyl acetate in hexane) to afford the title compound (0.17 g, 63%) as a white solid. MS: 322.2 (M+H⁻).

Intermediate A-6

5-Fluoro-1-methyl-6-(4,4,5,5-tetramethyl-1,3,2-dioxaborolan-2-yl)-3,4-dihydroquinolin-2-one

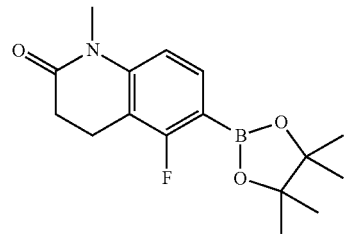 [SMILES: CN1C(=O)CCc2c1ccc(B1OC(C)(C)C(C)(C)O1)c2F]

[A] 2-(Bromomethyl)-1-fluoro-3-nitro-benzene

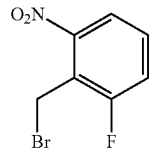 [SMILES: O=[N+]([O-])c1cccc(F)c1CBr]

To a stirred solution of 1-fluoro-2-methyl-3-nitro-benzene (100 g, 0.64 mol) and benzoyl peroxide (BPO) (15 g, 64 mmol) in CCl₄ (1500 mL) was added NBS (127 g, 0.73 mmol). The resulting reaction mixture was heated to reflux for 12 h at 80° C. After TLC (PE: EA=20:1) indicated the completion of reaction, the reaction mixture was concentrated to remove CCl₄. The residue was diluted with DCM (500 mL), and washed with brine (2×300 mL). The organic layer was dried over anhy. Na₂SO₄ and concentrated in vacuo to give a crude title product (160 g, 80%). It was used in the next step without further purification.

[B] Diethyl 2-[(2-fluoro-6-nitro-phenyl)methyl]propanedioate

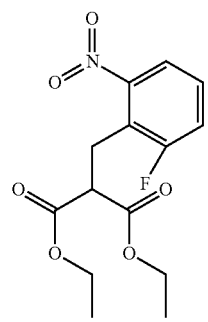 [SMILES: CCOC(=O)C(Cc1c(F)cccc1[N+](=O)[O-])C(=O)OCC]

To a stirred solution of NaH (26 g, 0.65 mol) in DMF (500 mL) was added diethyl malonate (106 g, 0.66 mol) in 200 mL of DMF at 0° C. It was stirred for 30 min at 0° C. before adding a solution of 2-(bromomethyl)-1-fluoro-3-nitro-benzene (128 g, 0.55 mol) in DMF (600 mL). The mixture was then allowed to warm up to room temperature and stirring was continued for 3 h before quenching by the addition of satd. aq. NH₄Cl (500 mL). The mixture was diluted with H₂O (2 L), and the aqueous layer was extracted with EtOAc (3×800 mL). The combined organics were washed with brine (3×500 mL), dried over anhy. Na₂SO₄ and concentrated in vacuo to give a crude title product (180 g, 70%). It was used in the next step without further purification.

[C] Ethyl 5-fluoro-2-oxo-3,4-dihydro-1H-quinoline-3-carboxylate

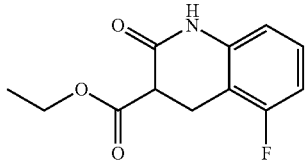 [SMILES: CCOC(=O)C1Cc2c(F)cccc2NC1=O]

To a stirred solution of diethyl 2-[(2-fluoro-6-nitro-phenyl)methyl]propanedioate (126 g, 0.4 mol) and NH₄Cl (103 g, 2.4 mol) in EtOH/H₂O (5:1, 1200 mL) was added iron powder (67 g, 1.2 mol) at 80° C. portion wise. The resulting mixture was refluxed for 2 h at 80° C. After cooling to room temperature, the reaction mixture was filtered and the filtrate was concentrated in vacuo to give a crude title product (92 g, 50%). MS: 238.1 (M+H⁺). It was used in the next step without further purification.

[D] 5-Fluoro-3,4-dihydro-1H-quinolin-2-one

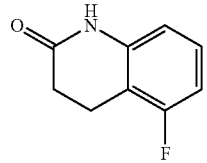 [SMILES: O=C1CCc2c(F)cccc2N1]

A solution of ethyl 5-fluoro-2-oxo-3,4-dihydro-1H-quinoline-3-carboxylate (46 g, 0.19 mol) in AcOH (300 mL) and HCl (150 mL) was heated to 90° C. for 1 h before it was concentrated under reduced pressure. Saturated aqueous Na₂CO₃ solution (500 mL) was carefully added to the residue, then it was diluted with additional H₂O (1 L), and extracted with EtOAc (3×300 mL). The combined organics were washed with brine (2×500 mL), dried over anhy. Na₂SO₄ and concentrated in vacuo to give a crude title product (28 g, 89.3%). MS: 166.1 (M+H⁻). It was used in the next step without further purification.

[E] 5-Fluoro-1-methyl-3,4-dihydroquinolin-2-one

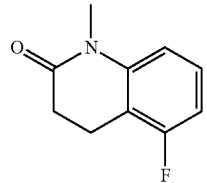

To a solution of NaH (8.1 g, 0.20 mol) in DMF (200 mL) was added 5-fluoro-3,4-dihydro-1H-quinolin-2-one (28 g, 0.17 mol) in 100 mL of DMF at 0° C. The resulting reaction mixture was stirred at 0° C. for 10 min before methyl iodide (30 g, 0.21 mmol) was added. After the addition, it was allowed to warm up to room temperature and stirred for 1 h. The reaction was then quenched by the addition of satd. aq. NH₄Cl (200 mL), diluted with H₂O (1 L), and extracted with EtOAc (3×300 mL). The combined organics were washed with brine (3×500 mL), dried over anhy. Na₂SO₄ and concentrated in vacuo to give crude title compound (32 g, 80%). MS: 180.1 (M+H⁻). It was used in the next step without further purification.

[F] 6-Bromo-5-fluoro-1-methyl-3,4-dihydroquinolin-2-one

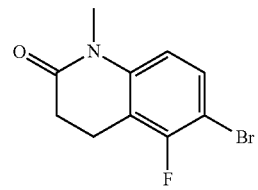

To a solution of 5-fluoro-1-methyl-3,4-dihydroquinolin-2-one (25.6 g, 0.14 mol) in DMF (300 mL) was added NBS (30 g, 0.17 mol) and the resulting reaction mixture was stirred at room temperature for 12 h. It was diluted with H₂O (800 mL), and the aqueous layer was extracted with EtOAc (3×200 mL). The combined organics were washed with brine (3×300 mL), dried over anhy. Na₂SO₄ and concentrated in vacuo to give crude title compound (15 g, 42%). MS: 256.1 and 258.1 (M+H⁺).

[G] 5-Fluoro-1-methyl-6-(4,4,5,5-tetramethyl-[1,3,2] dioxaborolan-2-yl)-3,4-dihydro-1H-quinolin-2-one

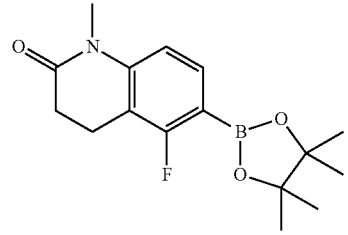 [SMILES: CN1C(=O)CCc2c1ccc(B1OC(C)(C)C(C)(C)O1)c2F]

A flask was charged with 6-bromo-5-fluoro-1-methyl-3,4-dihydroquinolin-2-one (14.5 g, 56 mmol), 4,4,4',4',5,5,5',5'-octamethyl-2,2'-bi(1,3,2-dioxaborolane) (28 g, 113 mmol), potassium acetate (11 g, 113 mmol) and DMSO (300 mL). The mixture was purged with Ar, then dichloro[1,1'-bis(diphenylphosphino)-ferrocene]palladium(II) dichloromethane complex (1:1) [PdCl₂(DPPF)-CH₂Cl₂ adduct] (2.2 g, 2.8 mmol) was added and the resulting mixture was heated to 80° C. for 3 h. The reaction mixture was filtered and the filtrate was diluted with satd. aq. NH₄Cl (200 mL) and H₂O (1 L). The aqueous layer was extracted with EtOAc (3×200 mL) and the combined organics were washed with brine (2×200 mL), dried over anhy. Na₂SO₄, filtered and evaporated to dryness. The residue was purified by silica gel flash chromatography eluting with a 0 to 20% EtOAc-heptane gradient to give the desired title compound (7.9 g, 46.5%) as an off white solid. MS: 306.0 (M+H⁺).

Intermediate A-7

5-Chloro-1-methyl-6-(4,4,5,5-tetramethyl-1,3,2-dioxaborolan-2-yl)-3,4-dihydroquinolin-2-one

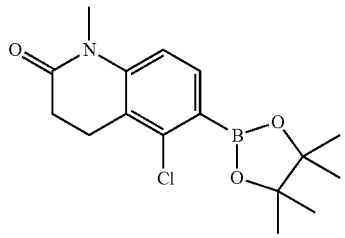 [SMILES: CN1C(=O)CCc2c1ccc(B1OC(C)(C)C(C)(C)O1)c2Cl]

[A] 2-(Bromomethyl)-1-chloro-3-nitro-benzene

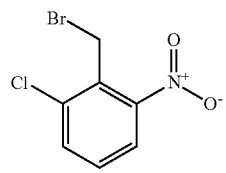 [SMILES: O=[N+]([O-])c1cccc(Cl)c1CBr]

A solution of 1-chloro-2-methyl-3-nitro-benzene (25.0 g, 145.7 mmol), N-bromosuccin-imide (30.0 g, 16.8 mmol) and benzoyl peroxide (2.5 g, 10.4 mmol) in carbon tetrachloride (300 mL) was heated to 100° C. for 10 h. After TLC indicated the reaction was completed, the reaction mixture was filtered and the filtrate was concentrated in vacuo to give crude product as yellow oil (40.0 g, 100%). MS: 250.1 (M+H)⁺. It was used in the next step without further purification.

[B] Diethyl 2-[(2-chloro-6-nitro-phenyl)methyl]propanedioate

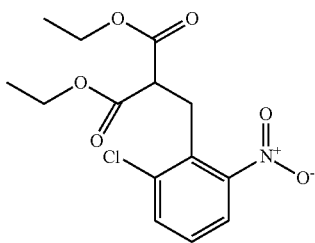 [SMILES: CCOC(=O)C(Cc1c(Cl)cccc1[N+](=O)[O-])C(=O)OCC]

A solution of 2-(bromomethyl)-1-chloro-3-nitro-benzene (50.0 g, 199.6 mmol), diethyl malonate (40.0 g, 260.0 mmol) and cesium carbonate (97.5 g, 300.0 mmol) in DMF (550 mL) was stirred at 0° C. for 10 min and then at room temperature for additional 2 h. The reaction was quenched by aq. 1 N HCl (300 mL), and the aqueous layer was extracted with diethyl ether (3×500 mL). After filtration, the organic layer was dried over anhy. Na₂SO₄, and concentrated in vacuo to give crude compound as yellow oil (68.0 g, 100%). MS: 330.1 (M+H)⁺. It was used in the next step without further purification.

[C] 5-Chloro-3,4-dihydro-1H-quinolin-2-one

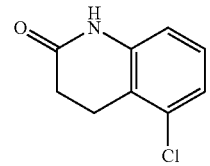 [SMILES: O=C1CCc2c(Cl)cccc2N1]

A solution of diethyl 2-[(2-chloro-6-nitro-phenyl)methyl]propanedioate (20 g, 61.9 mmol), stannous chloride dehydrate (100 g, 443.0 mmol) in 6 Naq. HCl (400 mL) was heated to 130° C. for 5 h. The reaction mixture was extracted with DCM (4×200 mL), and washed with brine. The organic layer was dried over anhy. Na₂SO₄, filtered, and concentrated in vacuo to afford crude title compound as a yellow solid (18.0 g, 80%). MS: 181.9 (M+H)⁺.

[D] 5-Chloro-1-methyl-3,4-dihydroquinolin-2-one

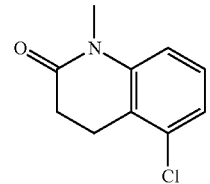

To a solution of 5-chloro-3,4-dihydro-1H-quinolin-2-one (16.0 g, 88.4 mmol), t-BuONa (16.0 g, 166.7 mmol) in THF (200 mL) was added methyl iodide (16.0 g, 140.4 mmol) drop wise at 0° C. After the addition, the reaction mixture was slowly warmed up to room temperature and stirred overnight. It was then quenched with satd. aq. NaCl solution, extracted with diethyl ether (200 mL×3), dried over anhy. Na₂SO₄, and concentrated in vacuo. The residue was purified by silica gel flash chromatography to afford the desired title compound as a pale yellow solid (16.0 g, 82%). MS: 196.1 (M+H)⁺.

[E] 6-Bromo-5-chloro-1-methyl-3,4-dihydroquinolin-2-one

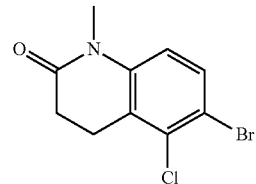

To a solution of 5-chloro-1-methyl-3,4-dihydroquinolin-2-one (15.2 g, 77.6 mmol) in DMF (250 mL) was added bromosuccinimide (15.2 g, 85.4 mmol) portion wise at 0° C. After the addition, the reaction mixture was allowed to warm up to room temperature and stirred overnight. The reaction was diluted with water (500 mL), extracted with diethyl ether (4×200 mL), dried over anhy. Na₂SO₄, and concentrated in vacuo. The residue was then purified by silica gel flash chromatography to afford the desired title compound as a brown solid (16.0 g, 75%). MS: 274.9 (M+H)⁺.

[F] 5-Chloro-1-methyl-6-(4,4,5,5-tetramethyl-[1,3,2] dioxaborolan-2-yl)-3,4-dihydro-1H-quinolin-2-one

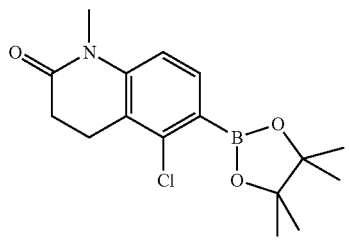 [SMILES: CN1C(=O)CCc2c1ccc(B1OC(C)(C)C(C)(C)O1)c2Cl]

A stirred solution of 6-bromo-5-chloro-1-methyl-3,4-dihydroquinolin-2-one (5.0 g, 18.2 mmol), bis(pinacolato) diboron (7.5 g, 29.5 mmol), PdCl$_2$(DPPF)-CH$_2$Cl$_2$ (1.0 g, 1.23 mmol), KOAc (6.0 g, 61.2 mmol) in degassed dioxane (100 mL) and DMSO (10 mL) was heated to 90° C. overnight. After cooling to room temperature, the reaction mixture was filtered and the filtrate was diluted with diethyl ether, washed with brine, dried over anhy. Na$_2$SO$_4$, and concentrated in vacuo to give a crude product, which was then purified by silica gel flash chromatography to afford desired title compound as a white solid (2.8 g, 47%). MS: 322.2(M+H)⁺.

Intermediate A-10

5-Iodo-4-[(4-methoxyphenyl)methoxy]-1H-pyrazole

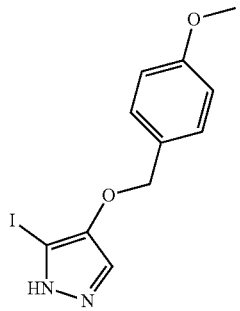

[A] 4-[(4-Methoxyphenyl)methoxy]-1H-pyrazole

To a solution of 1H-pyrazol-4-ol hydrochloride (1.00 g, 8.3 mmol) in DMF (20.0 mL) cooled to 0° C. were added tetrabutylammonium iodide (0.613 g, 1.66 mmol), NaH 60% in mineral oil (0.995 g, 24.9 mmol) and the reaction mixture was stirred for 30 min. Then, 4-methoxybenzylbromide (1.67 g, 8.3 mmol) was added drop wise to the mixture and stirring was continued at 0° C. for 30 min. The reaction mixture was treated with a sat. aqueous NH$_4$Cl solution (10 mL) and extracted with EtOAc (3×50 mL). The combined organics were dried over Na$_2$SO$_4$, filtered and evaporated. The residue was purified by silica gel flash chromatography, eluting with a 5% to 100% EtOAc-heptane gradient to give the title compound (1.02 g, 60%) as a colorless solid. MS: 205.1 (M+H⁺).

[B] 5-Iodo-4-[(4-methoxyphenyl)methoxy]-1H-pyrazole

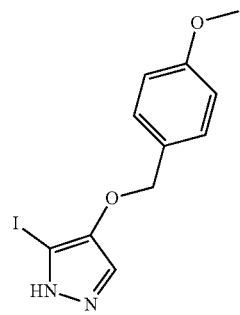 [SMILES: COc1ccc(COc2cn[nH]c2I)cc1]

To a solution of 4-(4-methoxybenzyloxy)-1H-pyrazole (1.02 g, 4.98 mmol) in DMF (15 mL) was added N-iodosuccinimide (1.23 g, 5.48 mmol) and the reaction mixture was heated to 60° C. for 2 h. The mixture was treated with H$_2$O (10 mL) and extracted with EtOAc (2×15 mL). The combined organics were dried over Na$_2$SO$_4$, filtered and evaporated. The residue was purified by silica gel flash chromatography, eluting with a 10% to 60% EtOAc-heptane gradient to give the title compound (1.11 g, 67.5%) as a colorless amorphous solid. MS: 331.0 (M+H⁺).

Intermediate A-11

[3-Iodo-1-(2-trimethylsilylethoxymethyl)pyrazol-4-yl]methanol

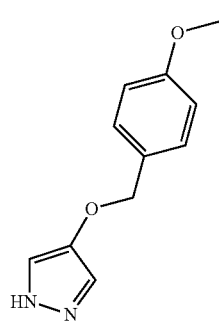

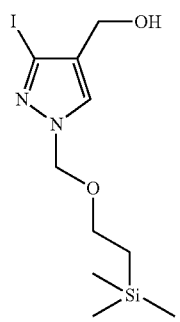 [SMILES: C[Si](C)(C)CCOCn1cc(CO)c(I)n1]

[A] Ethyl 3-iodo-1H-pyrazole-4-carboxylate

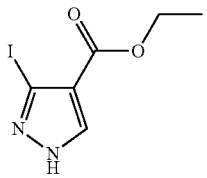

To a solution of ethyl 3-amino-1H-pyrazole-4-carboxylate (40 g, 0.258 mol) in MeCN (40 mL) was added isopentyl nitrite (36 g, 0.31 mol) and CH$_2$I$_2$ (207 g, 0.774 mol) at 0° C. The resulting mixture was stirred at 0° C. for 20 min and then heated to 100° C. for 12 h. After cooling to room temperature, the mixture was concentrated in vacuo and the residue was diluted with water and extracted with EtOAc (3×300 mL). The combined organics were washed with brine (3×200 mL), dried over anhy. Na$_2$SO$_4$, filtered, and concentrated in vacuo to give a crude product, which was purified by silica gel flash chromatography (PE: EA=2: 1) to give the desired title compound (40 g, 58%) as a yellow solid. MS: 267.1 (M+H$^+$).

[B] Ethyl 3-iodo-1-(2-trimethylsilylethoxymethyl)pyrazole-4-carboxylate

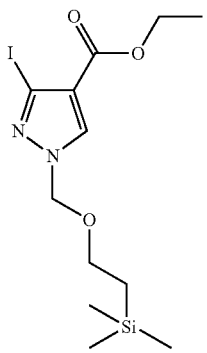 [SMILES: CCOC(=O)c1cn(COCC[Si](C)(C)C)nc1I]

To a solution of ethyl 3-iodo-1H-pyrazole-4-carboxylate (40 g, 150 mmol) in THF (500 mL) was added NaH (7.2 g, 180 mmol) portion wise at 0° C. The resulting mixture was stirred at 0° C. for 30 min before SEMCl (30 g, 180 mmol) was added drop wise. The mixture was then allowed to warm up to room temperature and stirred for 3 h before it was quenched with satd. aq. NH$_4$Cl (200 mL), and extracted with EtOAc (3×200 mL). The combined organics were washed with brine (3×200 mL), dried over anhy. Na$_2$SO$_4$, filtered, and concentrated in vacuo to give a crude product, which was purified by silica gel flash chromatography (PE: EA=2: 1) to afford the desired title compound (50 g, 84%) as a white solid. MS: 397.1 (M+H$^+$).

[C] [3-Iodo-1-(2-trimethylsilylethoxymethyl)pyrazol-4-yl]methanol

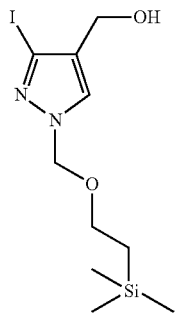 [SMILES: C[Si](C)(C)CCOCn1cc(CO)c(I)n1]

To a stirred solution of ethyl 3-iodo-1-(2-trimethylsilylethoxymethyl)pyrazole-4-carboxylate (50 g, 126 mmol) in THF (600 mL) was added DIBAL (379 mL, 379 mmol) at −78° C. and the resulting mixture was stirred at −78° C. for 3 h before was warmed up to room temperature and quenched by the addition of a satd. Seignette salt solution (600 mL). After dilution with H$_2$O (1 L), the aqueous layer was extracted with EtOAc (3×300 mL). The combined organics were washed with brine (3×200 mL), dried over anhy. Na$_2$SO$_4$ filtered, and concentrated in vacuo to give a crude product, which was purified by silica gel flash chromatography (PE: EA=2:1) to afford the desired title compound (28 g, 63%) as yellow oil. MS: 355.1 (M+H$^+$).

Example 1

4-[[5-(1-Methyl-2-oxo-3,4-dihydroquinolin-6-yl)-1H-pyrazol-4-yl]oxy]benzonitrile

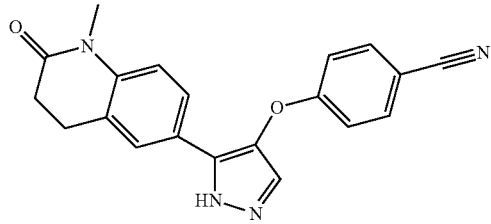 [SMILES: CN1C(=O)CCc2cc(-c3[nH]ncc3Oc3ccc(C#N)cc3)ccc21]

To a solution of 4-[(Z and/or E)-2-(dimethylamino)-1-(1-methyl-2-oxo-3,4-dihydroquinoline-6-carbonyl)vinyloxy]benzonitrile (intermediate A-1) (0.075 g, 0.2 mmol) in EtOH (2 mL) was added hydrazine monohydrate (0.011 g, 0.22 mmol) followed by a 4M HCl in dioxane solution (0.05 ml, 0.2 mmol) and the reaction mixture was then heated to 80° C. overnight. The mixture was evaporated to dryness and the residue purified by silica gel flash chromatography eluting with a 0 to 5% MeOH-dichloromethane gradient to give the title compound (0.051 g, 71%) as a light yellow solid. MS: 345.4 (M+H$^+$).

The following examples listed in Table 1 were prepared from 6-(2-bromoacetyl)-1-methyl-3,4-dihydroquinolin-2-one and a suitable phenol in analogy to the procedures described for the preparation of intermediate A-1 and example 1:

TABLE 1

| Example | Name / Aspect | Reactant (phenol) | MS (M + H⁺) |
|---|---|---|---|
| 2 | 6-[4-(4-Chlorophenoxy)-1H-pyrazol-5-yl]-1-methyl-3,4-dihydroquinolin-2-one 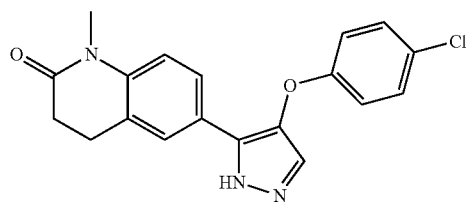 yellow solid | 4-chlorophenol | 354.4 |
| 3 | 3-Methoxy-4-[[5-(1-methyl-2-oxo-3,4-dihydroquinolin-6-yl)-1H-pyrazol-4-yl]oxy]benzonitrile 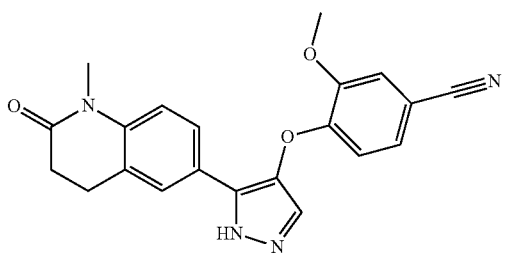 colorless amorphous solid | 4-hydroxy-3-methoxy-benzonitrile | 375.6 |
| 4 | 3-Chloro-4-[[5-(1-methyl-2-oxo-3,4-dihydroquinolin-6-yl)-1H-pyrazol-4-yl]oxy]benzonitrile 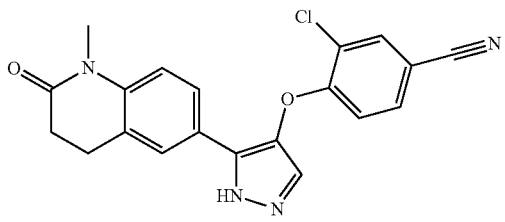 off-white solid | 3-chloro-4-hydroxy-benzonitrile | 379.6 |
| 5 | 2-Fluoro-4-[[5-(1-methyl-2-oxo-3,4-dihydroquinolin-6-yl)-1H-pyrazol-4-yl]oxy]benzonitrile 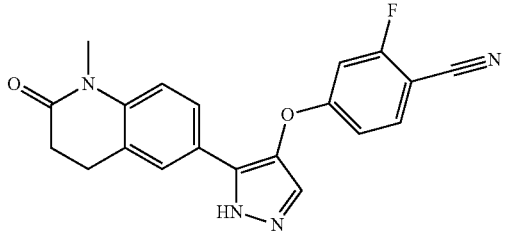 colorless solid | 2-fluoro-4-hydroxy-benzonitrile | 363.4 |

TABLE 1-continued

| Example | Name Aspect | Reactant (phenol) | MS (M + H+) |
|---|---|---|---|
| 6 | 2-Chloro-4-[[5-(1-methyl-2-oxo-3,4-dihydroquinolin-6-yl)-1H-pyrazol-4-yl]oxy]benzonitrile<br>light yellow solid | 2-chloro-4-hydroxy-benzonitrile | 379.5 |
| 7 | 6-[4-(3-Chlorophenoxy)-1H-pyrazol-5-yl]-1-methyl-3,4-dihydroquinolin-2-one<br>off-white solid | 3-chloro-phenol | 354.5 |
| 8 | 1-Methyl-6-[4-(4-methylsulfanylphenoxy)-1H-pyrazol-5-yl]-3,4-dihydroquinolin-2-one<br>light yellow solid | 4-methylsulfanyl-phenol | 366.5 |
| 9 | 1-Methyl-6-[4-(3-methylsulfanylphenoxy)-1H-pyrazol-5-yl]-3,4-dihydroquinolin-2-one<br>yellow solid | 3-methylsulfanyl-phenol | 366.5 |

Example 10

1-Methyl-6-[4-(3-methylsulfonylphenoxy)-1H-pyrazol-5-yl]-3,4-dihydroquinolin-2-one

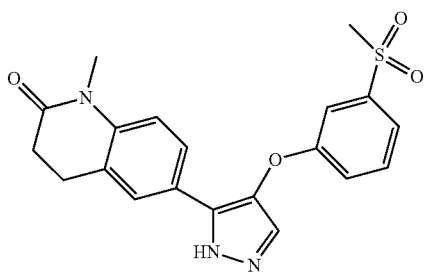 [SMILES: CN1C(=O)CCc2cc(-c3[nH]ncc3Oc3cccc(S(C)(=O)=O)c3)ccc21]

Sodium bicarbonate (0.101 g, 1.2 mmol) in water (1 mL) was added at 0° C. (ice bath) to a solution of 1-methyl-6-[4-(3-methylsulfanylphenoxy)-1H-pyrazol-5-yl]-3,4-dihydroquinolin-2-one (example 9) (0.055 g, 0.150 mmol) in acetone (1 mL). A solution of oxone (0.13 g, 0.211 mmol) in water (1.5 mL) was added drop wise to the mixture while keeping the temperature below 5° C. and stirring was continued at this temperature for 30 min and then at room temperature for 1 h. The mixture was quenched at 0° C. by addition of a 40% sodium bisulfite solution (2 mL). The resulting suspension was diluted with EtOAc, acidified with a 25% aqueous HCl solution and the resulting aqueous layer was extracted with EtOAc (2×10 mL). The combined organics were washed with brine, dried over $Na_2SO_4$, filtered and evaporated. The residue was purified by prep-HPLC (Gemini NX 3u column, gradient 1% aq. formic acid/acetonitrile) to give the title compound (0.03 g, 48%) as a yellow amorphous solid. MS: 398.5 (M+H$^+$).

Example 11

1-Methyl-6-[4-(4-methylsulfonylphenoxy)-1H-pyrazol-5-yl]-3,4-dihydroquinolin-2-one

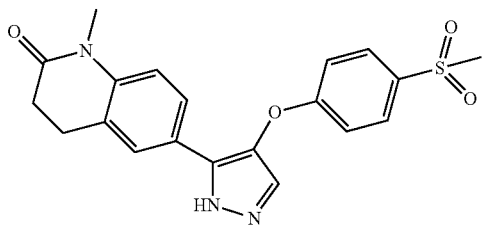 [SMILES: CN1C(=O)CCc2cc(-c3[nH]ncc3Oc3ccc(S(C)(=O)=O)cc3)ccc21]

In analogy to the procedure described in example 10, 1-methyl-6-[4-(4-methylsulfanylphenoxy)-1H-pyrazol-5-yl]-3,4-dihydroquinolin-2-one (example 8) has been oxidized with oxone to give the title compound as a colorless amorphous solid. MS: 398.6 (M+H$^+$).

Example 12

1-Methyl-6-[4-(2-methylsulfanylethoxymethyl)-1H-pyrazol-3-yl]-3,4-dihydroquinolin-2-one

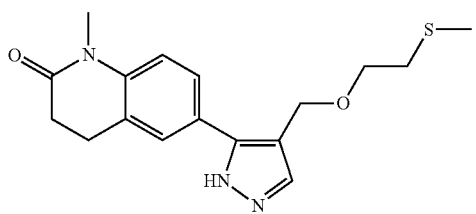 [SMILES: CSCCOCc1cn[nH]c1-c1ccc2c(c1)CCC(=O)N2C]

To a solution of (rac)-1-methyl-6-[4-(2-methylsulfanylethoxymethyl)-1-tetrahydropyran-2-yl-pyrazol-3-yl]-3,4-dihydroquinolin-2-one (intermediate A-2) (0.015 g, 0.036 mmol) in MeOH (1 mL) was added a 4M HCl in dioxane solution (0.045 ml, 0.18 mmol) and the reaction mixture was stirred at room temperature for 3 h. The mixture was evaporated to dryness, the residue treated with a sat. $NaHCO_3$ solution (1 mL) and then extracted with EtOAc (2×5 mL). The organic layers were dried over $Na_2SO_4$, filtered and evaporated to give the title compound (0.012 g, 97%) as a light brown amorphous solid. MS: 332.2 (M+H$^+$).

Example 13

(rac)-1-Methyl-6-[4-(1-methylsulfanylpropan-2-yloxymethyl)-1H-pyrazol-3-yl]-3,4-dihydroquinolin-2-one

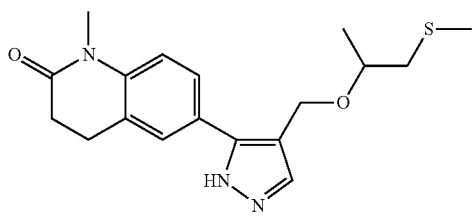 [SMILES: CSCC(C)OCc1cn[nH]c1-c1ccc2c(c1)CCC(=O)N2C]

In analogy to the procedure described in example 12, 1-methyl-6-[4-[(1-methyl-2-methylsulfanyl-ethoxy)methyl]-1-tetrahydropyran-2-yl-pyrazol-3-yl]-3,4-dihydroquinolin-2-one (as 2 racemic diastereomers) (prepared from (rac)-4-(chloromethyl)-3-iodo-1-(tetrahydro-2H-pyran-2-yl)-1H-pyrazole (intermediate A-2 [C] and (rac)-1-methylsulfanylpropan-2-ol in analogy to the procedures described for the preparation of intermediates A-2[D-E]) has been treated with acid to give the title compound as a colorless oil. MS: 346.2 (M+H$^+$).

Example 14

1-Methyl-6-[4-(2-methylsulfonylethoxymethyl)-1H-pyrazol-3-yl]-3,4-dihydroquinolin-2-one

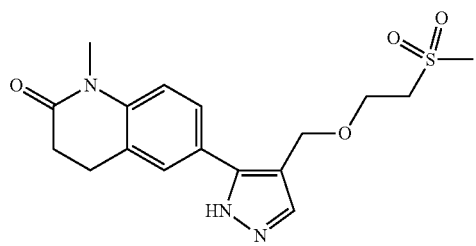 [SMILES: CN1C(=O)CCc2cc(-c3[nH]ncc3COCCS(C)(=O)=O)ccc21]

In analogy to the procedure described in example 10, 1-methyl-6-[4-(2-methylsulfanylethoxymethyl)-1H-pyrazol-3-yl]-3,4-dihydroquinolin-2-one (example 12) has been oxidized with oxone to give the title compound as an off-white amorphous solid. MS: 364.2 (M+H$^+$).

Example 15

6-[4-[(4-Methoxyphenyl)methoxy]-1H-pyrazol-3-yl]-1-methyl-3,4-dihydroquinolin-2-one

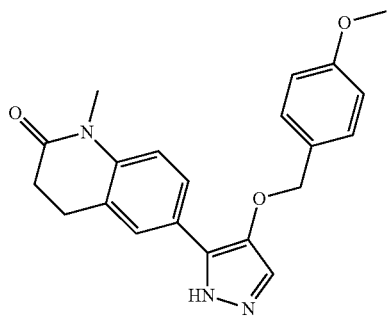 [SMILES: COc1ccc(COc2cn[nH]c2-c2ccc3c(c2)CCC(=O)N3C)cc1]

To a solution of 5-iodo-4-[(4-methoxyphenyl)methoxy]-1H-pyrazole (intermediate A-10) (0.4 g, 1.21 mmol) in DMF (4 mL) were added 1-methyl-6-(4,4,5,5-tetramethyl-1,3,2-dioxaborolan-2-yl)-3,4-dihydroquinolin-2(1H)-one (0.348 g, 1.21 mmol), bis(diphenylphosphino)ferrocenedichloropalladium (II) (0.085 g, 0.121 mmol) and a 1M aqueous Na$_2$CO$_3$ solution (3.64 mL, 3.64 mmol). The reaction mixture was then heated to 120° C. for 1 h under microwave irradiation. The mixture was poured into a sat. aqueous NaHCO$_3$ solution (2 mL) and extracted with EtOAc (2×10 mL). The combined organics were washed with brine, dried over Na$_2$SO$_4$, filtered and evaporated. The residue was purified by silica gel flash chromatography eluting with a 10 to 100% EtOAc-heptane gradient to give the title compound (0.14 g, 30%) as a light yellow solid. MS: 364.2 (M+H$^+$).

Example 65

6-[4-[[1-(3-Chloropyridine-2-carbonyl)azetidin-3-yl]oxymethyl]-1H-pyrazol-3-yl]-5-fluoro-1-methyl-3,4-dihydroquinolin-2-one

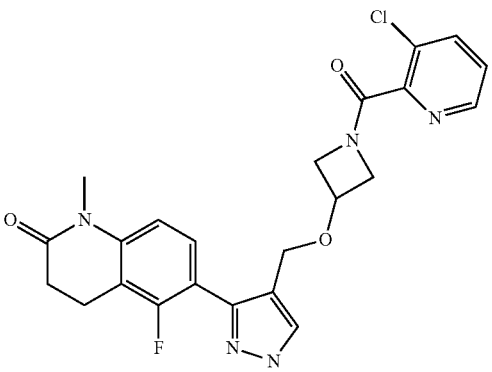 [SMILES: CN1C(=O)CCc2c1ccc(-c1n[nH]cc1COC1CN(C(=O)c3ncccc3Cl)C1)c2F]

[A] 2-[[4-(Bromomethyl)-3-iodo-pyrazol-1-yl]methoxy]ethyl-trimethyl-silane

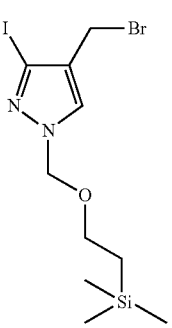 [SMILES: C[Si](C)(C)CCOCn1cc(CBr)c(I)n1]

To a stirred solution of [3-iodo-1-(2-trimethylsilylethoxymethyl)pyrazol-4-yl]methanol (2 g, 5.6 mmol, intermediate A-11]) in DCM (30 mL) was added PBr$_3$ (750 mg, 2.8 mmol) drop wise at 0° C. and stirring was continued for 1 h. The reaction was then quenched by satd. aq. NaHCO$_3$ (20 mL), diluted with H$_2$O (50 mL), and extracted with DCM (3×10 mL). The combined organics were washed with brine (2×20 mL), dried over anhy. Na$_2$SO$_4$, filtered, and concentrated in vacuo to give a crude product (1.2 g, 41%). MS: 417.1 (M+H$^+$). It was used in the next step without further purification.

[B] tert-Butyl 3-[[3-iodo-1-(2-trimethylsilylethoxymethyl)pyrazol-4-yl]methoxy]azetidine-1-carboxylate

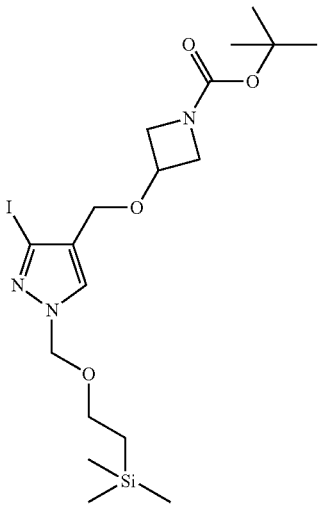 [SMILES: CC(C)(C)OC(=O)N1CC(OCc2cn(COCC[Si](C)(C)C)nc2I)C1]

To a solution of NaH (110 mg, 2.8 mmol) in THF (20 mL) was added tert-butyl 3-hydroxyazetidine-1-carboxylate (485 mg, 2.8 mmol) at 0° C. and it was stirred for 30 min before 2-[[4-(bromomethyl)-3-iodo-pyrazol-1-yl]methoxy]ethyl-trimethyl-silane (1.2 g, 2.3 mmol) was added. This resulting mixture was allowed to warm up to room temperature and stirred overnight. The reaction was then quenched by satd. aq. NH$_4$Cl (30 mL), diluted with H$_2$O (80 mL), and extracted with EtOAc (3×20 mL). The combined organics were washed with brine (2×30 mL), dried over anhy. Na$_2$SO$_4$, filtered, and concentrated in vacuo to give a crude product, which was purified by silica gel flash chromatography (PE: EA=2:1) to afford the desired title compound (0.8 g, 68%) as yellow oil. MS: 510.1 (M+H$^+$).

[C] tert-Butyl 3-[[3-(5-fluoro-1-methyl-2-oxo-3,4-dihydroquinolin-6-yl)-1-(2-trimethylsilylethoxymethyl)pyrazol-4-yl]methoxy]azetidine-1-carboxylate

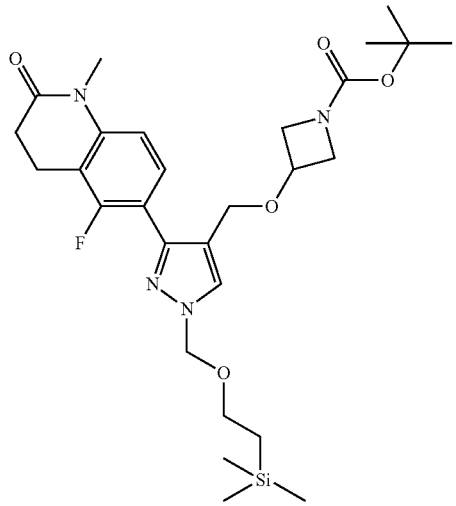 [SMILES: CN1C(=O)CCc2c1ccc(-c1nn(COCC[Si](C)(C)C)cc1COC1CN(C(=O)OC(C)(C)C)C1)c2F]

To a solution of tert-butyl 3-[[3-iodo-1-(2-trimethylsilylethoxymethyl)pyrazol-4-yl]methoxy]azetidine-1-carboxylate (800 mg, 1.57 mmol), Cs$_2$CO$_3$ (1 g, 3.1 mmol) and 5-fluoro-1-methyl-6-(4,4,5,5-tetramethyl-[1,3,2]dioxaborolan-2-yl)-3,4-dihydro-1H-quinolin-2-one (478 mg, 1.57 mmol) (intermediate A-6) in dioxane/H$_2$O (15:1, 32 mL) was added PdCl$_2$(DPPF) (110 mg, 0.15 mmol) under N$_2$. The resulting solution was heated to 80° C. for 3 h. After cooling to room temperature, the reaction was quenched with satd. aq. NH$_4$Cl solution (40 mL), diluted with H$_2$O (50 mL), and extracted with EtOAc (3×20 mL). The combined organics were washed with brine (2×20 mL), dried over anhy. Na$_2$SO$_4$, filtered, and concentrated in vacuo to give a crude product, which was purified by silica gel flash chromatography (DCM: MeOH=40:1) to afford the desired title compound (680 mg, 77%) as yellow oil. MS: 561.2 (M+H$^+$).

[D] 6-[4-(Azetidin-3-yloxymethyl)-1-(2-trimethylsilylethoxymethyl)pyrazol-3-yl]-5-fluoro-1-methyl-3,4-dihydroquinolin-2-one

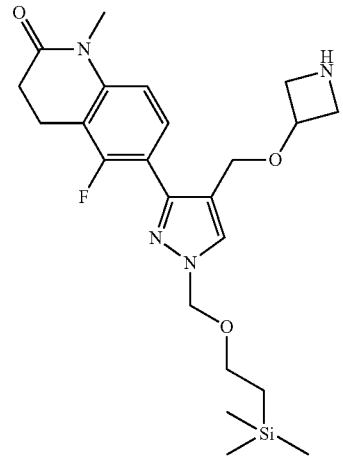 [SMILES: CN1C(=O)CCc2c1ccc(-c1nn(COCC[Si](C)(C)C)cc1COC1CNC1)c2F]

To a solution of tert-butyl 3-[[3-(5-fluoro-1-methyl-2-oxo-3,4-dihydroquinolin-6-yl)-1-(2-trimethylsilylethoxymethyl)pyrazol-4-yl]methoxy]azetidine-1-carboxylate (680 mg, 1.2 mmol) in EtOAc (10 mL) was added 4 M HCl in EtOAc (5 mL) at room temperature. The reaction mixture was stirred for 30 min before it was concentrated in vacuo to give a crude product (560 mg, 93%). MS: 461.2 (M+H$^+$). It was used in the next step without further purification.

[E] 6-[4-[[1-(3-Chloropyridine-2-carbonyl)azetidin-3-yl]oxymethyl]-1-(2-trimethylsilylethoxymethyl)pyrazol-3-yl]-5-fluoro-1-methyl-3,4-dihydroquinolin-2-one

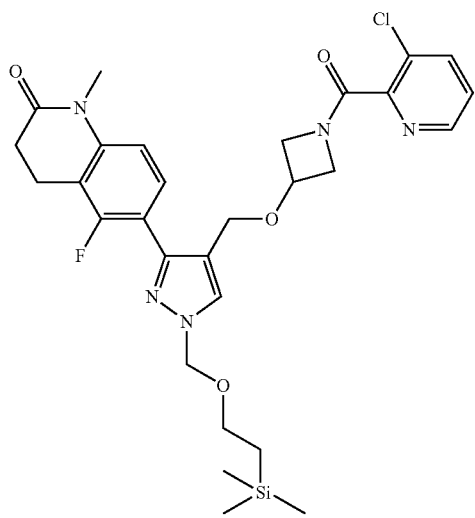 [SMILES: CN1C(=O)CCc2c1ccc(-c1nn(COCC[Si](C)(C)C)cc1COC1CN(C(=O)c3ncccc3Cl)C1)c2F]

To a solution of 6-[4-(azetidin-3-yloxymethyl)-1-(2-trimethylsilylethoxymethyl)-pyrazol-3-yl]-5-fluoro-1-methyl-3,4-dihydroquinolin-2-one (200 mg, 0.43 mmol), EDCI (100 mg, 0.52 mmol) and HOBT (70 mg, 0.52 mmol) in DCM (15 mL) was added 3-chloropyridine-2-carboxylic acid (67 mg, 0.43 mmol) and DIPEA (110 mg, 0.86 mmol). The resulting reaction mixture was stirred at room temperature for 3 h before it was quenched with satd. aq. NH$_4$Cl (20 mL), diluted with H$_2$O (50 mL), and extracted with DCM (3×10 mL). The combined organics were washed with brine (2×20 mL), dried over anhy. Na$_2$SO$_4$, filtered, and concentrated in vacuo to give a crude product, which was purified by silica gel flash chromatography (DCM: MeOH=40:1) to afford the desired title compound (100 mg, 42%) as yellow oil. MS: 600.2 (M+H$^+$).

[F] 6-[4-[[1-(3-Chloropyridine-2-carbonyl)azetidin-3-yl]oxymethyl]-1H-pyrazol-3-yl]-5-fluoro-1-methyl-3,4-dihydroquinolin-2-one

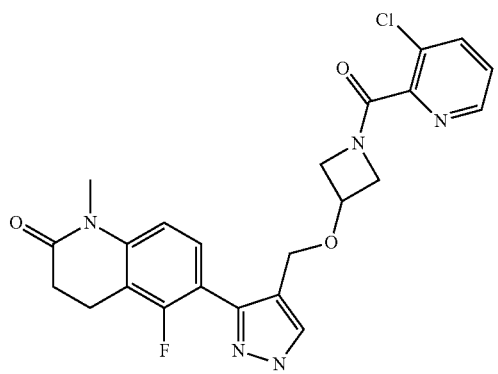 [SMILES: CN1C(=O)CCc2c1ccc(-c1n[nH]cc1COC1CN(C(=O)c3ncccc3Cl)C1)c2F]

A solution of 6-[4-[[1-(3-chloropyridine-2-carbonyl)azetidin-3-yl]oxymethyl]-1-(2-trimethylsilylethoxymethyl)pyrazol-3-yl]-5-fluoro-1-methyl-3,4-dihydroquinolin-2-one (100 mg, 0.17 mmol) in TFA (10 mL) was stirred at room temperature for 1 h. The reaction was quenched by satd. aq. NaHCO$_3$ solution (30 mL), diluted with H$_2$O (50 mL), and extracted with EtOAc (3×20 mL). The combined organics were washed with brine (2×20 mL), dried over anhy. Na$_2$SO$_4$, filtered, and concentrated in vacuo to give a crude product, which was purified by silica gel flash chromatography (DCM: MeOH=40: 1) to afford the desired title compound (35 mg, 45%) as yellow oil. MS: 470.1 (M+H$^+$).

Example 66

5-Fluoro-1-methyl-6-[4-[[1-(1-methylpyrazole-4-carbonyl)azetidin-3-yl]oxymethyl]-1H-pyrazol-3-yl]-3,4-dihydroquinolin-2-one

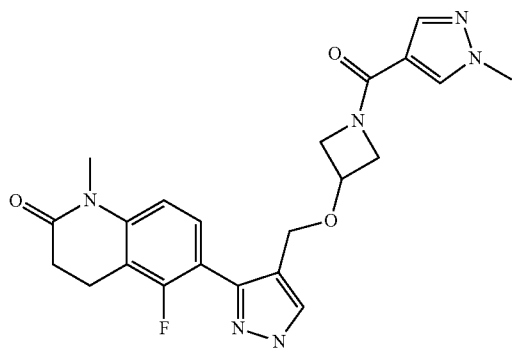 [SMILES: CN1C(=O)CCc2c1ccc(-c1n[nH]cc1COC1CN(C(=O)c3cnn(C)c3)C1)c2F]

[A] 5-Fluoro-1-methyl-6-[4-[[1-(1-methylpyrazole-4-carb onyl)azetidin-3-yl]oxymethyl]-1-(2-trimethylsilylethoxymethyl)pyrazol-3-yl]-3,4-dihydroquinolin-2-one

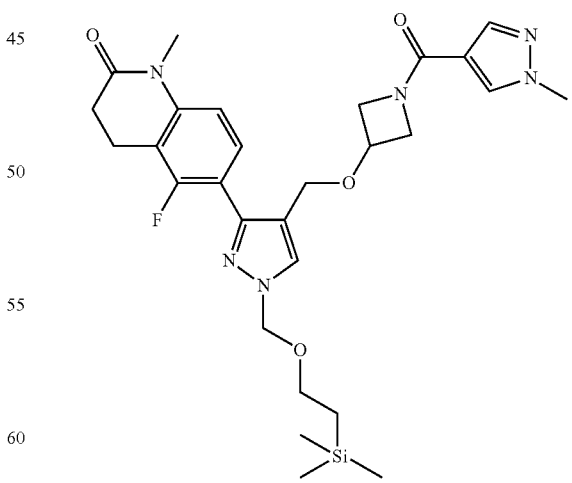

In analogy to the procedure described for the synthesis of example 65[E], 1-methylpyrazole-4-carboxylic acid was used to give the desired title compound (120 mg, 35%) as yellow oil. MS: 569.2 (M+H$^+$).

[B] 5-Fluoro-1-methyl-6-[4-[[1-(1-methylpyrazole-4-carbonyl)azetidin-3-yl]oxymethyl]-1H-pyrazol-3-yl]-3,4-dihydroquinolin-2-one

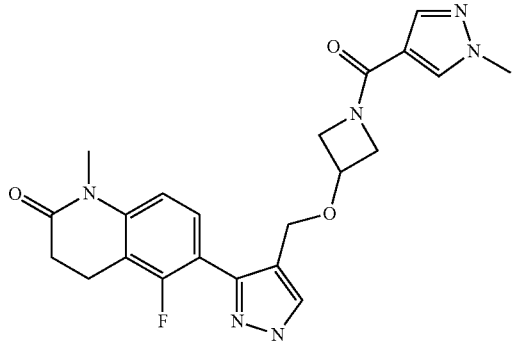 [SMILES: CN1C(=O)CCc2c1ccc(-c1n[nH]cc1COC1CN(C(=O)c3cnn(C)c3)C1)c2F]

In analogy to the procedure described for the synthesis of Example 65[F], 5-fluoro-1-methyl-6-[4-[[1-(1-methylpyrazole-4-carbonyl)azetidin-3-yl]oxymethyl]-1-(2-trimethylsilylethoxymethy)pyrazol-3-yl]-3,4-dihydroquinolin-2-one was used to give the desired title compound (43 mg, 47%) as yellow oil. MS: 439.2 (M+H$^+$).

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:
1. A compound of formula (I)

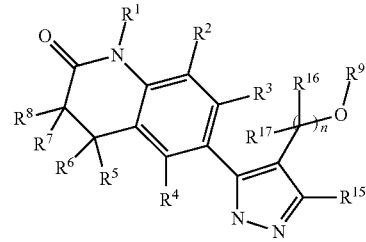

wherein
R$^1$, R$^5$, R$^6$, R$^7$ and R$^8$ are independently selected from H, alkyl, haloalkyl, cycloalkyl or halocycloalkyl;
R$^2$, R$^3$ and R$^4$ are independently selected from H, halogen, alkyl, haloalkyl, cycloalkyl or halocycloalkyl;
R$^9$ is alkylsulfanylalkyl, alkylsulfonylalkyl, aryl, substituted aryl, arylalkyl, substituted arylalkyl, heteroaryl, substituted heteroaryl, hetroarylalkyl, substituted heteroarylalkyl or the group A, wherein substituted aryl, substituted arylalkyl, substituted heteroaryl and substituted heteroarylalkyl are substituted with one to three substituents selected from the group consisting of alkyl, halogen, haloalkyl, cycloalkyl, halocycloalkyl, cyano, alkoxy, haloalkoxy, alkylsulfanyl, haloalkylsulfanyl, alkylsulfonyl and haloalkylsulfonyl;

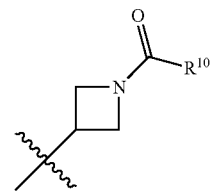

R$^{10}$ is pyrazolyl, substituted pyrazolyl, pyridinyl or substituted pyridinyl, wherein substituted pyrazolyl and substituted pyridinyl are substituted with one to three substituents selected from the group consisting of alkyl, halogen, haloalkyl, cycloalkyl and halocycloalkyl;
R$^{15}$ is H, alkyl, haloalkyl, cycloalkyl or halocycloalkyl;
R$^{16}$ and R$^{17}$ are independently selected from H, alkyl and cycloalkyl;
n is zero or 1;
or, pharmaceutically acceptable salts thereof.
2. The compound according to claim 1, wherein R$^1$ is alkyl.
3. The compound according to claim 1, wherein R$^5$, R$^6$, R$^7$ and R$^8$ are H.
4. The compound according to claim 1 wherein R$^2$ and R$^3$ are H.
5. The compound according to claim 1 wherein R$^4$ is H or halogen.
6. The compound according to claim 1, wherein R$^4$ is H.
7. The compound according to claim 1 wherein R$^{15}$ is H.
8. The compound according to claim 1, wherein R$^{16}$ and R$^{17}$ are H.
9. The compound according to claim 1 wherein n is 0.
10. The compound according to claim 1 wherein R$^1$ is alkyl, R$^2$, R$^3$, R$^5$, R$^6$, R$^7$, R$^8$, R$^{15}$, R$^{16}$ and R$^{17}$ are H, R$^4$ is H or halogen and n is 0.

11. The compound according to claim 10, wherein $R^9$ is alkylsulfanylalkyl, alkylsulfonylalkyl, substituted aryl, substituted arylalkyl or the group A, wherein substituted aryl and substituted arylalkyl are substituted with one to three substituents selected from alkyl, halogen, cyano, alkoxy, alkylsulfanyl and alkylsulfonyl.

12. The compound according to claim 1, wherein $R^9$ is alkylsulfanylalkyl, alkylsulfonylalkyl, substituted aryl, substituted arylalkyl or the group A, wherein substituted aryl and substituted arylalkyl are substituted with one to three substituents selected from alkyl, halogen, cyano, alkoxy, alkylsulfanyl and alkylsulfonyl.

13. The compound according to claim 1 wherein $R^{10}$ is either pyrazolyl substituted by one alkyl or pyridinyl substituted by one halogen.

14. The compound of claim 11 wherein $R^9$ is the group A and $R^{10}$ is either pyrazolyl substituted by one alkyl or pyridinyl substituted by one halogen.

15. The compound according to claim 1 wherein $R^9$ is aryl substituted with one to three substituents selected from alkyl, halogen, cyano, alkoxy, alkylsulfanyl and alkylsulfonyl.

16. The compound according to claim 11 wherein $R^9$ is aryl substituted with one to three substituents selected from alkyl, halogen, cyano, alkoxy, alkylsulfanyl and alkylsulfonyl.

17. The compound according to claim 1, which compound is selected from the group consisting of:
4-[[5-(1-Methyl-2-oxo-3,4-dihydroquinolin-6-yl)-1H-pyrazol-4-yl]oxy]benzonitrile;
6-[4-(4-Chlorophenoxy)-1H-pyrazol-5-yl]-1-methyl-3,4-dihydroquinolin-2-one;
3-Methoxy-4-[[5-(1-methyl-2-oxo-3,4-dihydroquinolin-6-yl)-1H-pyrazol-4-yl]oxy]benzonitrile;
3-Chloro-4-[[5-(1-methyl-2-oxo-3,4-dihydroquinolin-6-yl)-1H-pyrazol-4-yl]oxy]benzonitrile;
2-Fluoro-4-[[5-(1-methyl-2-oxo-3,4-dihydroquinolin-6-yl)-1H-pyrazol-4-yl]oxy]benzonitrile;
2-Chloro-4-[[5-(1-methyl-2-oxo-3,4-dihydroquinolin-6-yl)-1H-pyrazol-4-yl]oxy]benzonitrile;
6-[4-(3-Chlorophenoxy)-1H-pyrazol-5-yl]-1-methyl-3,4-dihydroquinolin-2-one;
1-Methyl-6-[4-(4-methylsulfanylphenoxy)-1H-pyrazol-5-yl]-3,4-dihydroquinolin-2-one;
1-Methyl-6-[4-(3-methylsulfanylphenoxy)-1H-pyrazol-5-yl]-3,4-dihydroquinolin-2-one;
1-Methyl-6-[4-(3-methylsulfonylphenoxy)-1H-pyrazol-5-yl]-3,4-dihydroquinolin-2-one;
1-Methyl-6-[4-(4-methylsulfonylphenoxy)-1H-pyrazol-5-yl]-3,4-dihydroquinolin-2-one;
1-Methyl-6-[4-(2-methylsulfanylethoxymethyl)-1H-pyrazol-3-yl]-3,4-dihydroquinolin-2-one;
(rac)-1-Methyl-6-[4-(1-methylsulfanylpropan-2-yloxymethyl)-1H-pyrazol-3-yl]-3,4-dihydroquinolin-2-one;
1-Methyl-6-[4-(2-methylsulfonylethoxymethyl)-1H-pyrazol-3-yl]-3,4-dihydroquinolin-2-one;
6-[4-[(4-Methoxyphenyl)methoxy]-1H-pyrazol-3-yl]-1-methyl-3,4-dihydroquinolin-2-one;
6-[4-[[1-(3-Chloropyridine-2-carbonyl)azetidin-3-yl]oxymethyl]-1H-pyrazol-3-yl]-5-fluoro-1-methyl-3,4-dihydroquinolin-2-one; and,
5-Fluoro-1-methyl-6-[4-[[1-(1-methylpyrazole-4-carbonyl)azetidin-3-yl]oxymethyl]-1H-pyrazol-3-yl]-3,4-dihydroquinolin-2-one; or,
a pharmaceutically acceptable salt thereof.

18. A process to prepare a compound according to to claim 1 comprising the reaction of a compound of formula (II) in the presence of hydrazine hydrate;

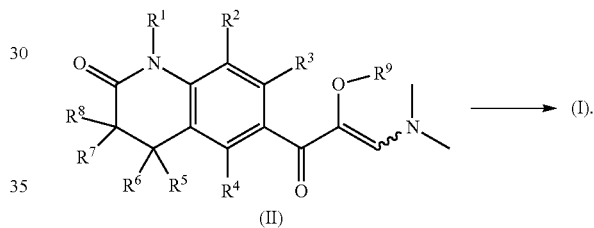

19. A pharmaceutical composition comprising a compound according to claim 1 and at least one pharmaceutically acceptable carrier, diluent or excipient.

* * * * *